(12) United States Patent
Wang et al.

(10) Patent No.: US 10,961,546 B2
(45) Date of Patent: Mar. 30, 2021

(54) GLYPHOSATE-RESISTANT GENE SCREENING METHOD, EPSPS MUTANT GENE AND DEFICIENT STRAIN AND USE

(71) Applicant: GEVOTO LLC, Sichuan (CN)

(72) Inventors: Boya Wang, Sichuan (CN); Yuangen Lu, Sichuan (CN); Nanfei Xu, Sichuan (CN)

(73) Assignee: GEVOTO LLC, Sichuan (CN)

( * ) Notice: Subject to any disclaimer, the term of this patent is extended or adjusted under 35 U.S.C. 154(b) by 173 days.

(21) Appl. No.: 16/194,010

(22) Filed: Nov. 16, 2018

(65) Prior Publication Data

US 2019/0144882 A1   May 16, 2019

Related U.S. Application Data

(63) Continuation-in-part of application No. PCT/CN2016/082409, filed on May 17, 2016.

(51) Int. Cl.

| | | |
|---|---|---|
| C12N 9/10 | (2006.01) | |
| C12N 15/82 | (2006.01) | |
| C12N 15/70 | (2006.01) | |
| C12Q 1/68 | (2018.01) | |
| C12N 9/88 | (2006.01) | |
| C12N 15/52 | (2006.01) | |
| C12Q 1/686 | (2018.01) | |
| C12Q 1/6895 | (2018.01) | |

(52) U.S. Cl.
CPC ....... *C12N 15/8275* (2013.01); *C12N 9/1092* (2013.01); *C12N 9/88* (2013.01); *C12N 15/52* (2013.01); *C12N 15/70* (2013.01); *C12N 15/8213* (2013.01); *C12Q 1/68* (2013.01); *C12Q 1/686* (2013.01); *C12Q 1/6895* (2013.01); *C12Y 205/01019* (2013.01)

(58) Field of Classification Search
CPC .................................................... C12N 9/1092
See application file for complete search history.

(56) References Cited

FOREIGN PATENT DOCUMENTS

| CN | 104099363 | 10/2014 |
|---|---|---|
| CN | 105063068 | 11/2015 |
| WO | WO 98/44140 | * 10/1998 |

OTHER PUBLICATIONS

Hove-Jensen et al Journal of Bacteriology vol. 192, No. 1, pp. 370-374 (Year: 2010).*
Tian et al Appl. Microbiol. Biotechnol vol. 93, pp. 241-250 (Year: 2012).*
Fan et al Gen. Appl. Microbiol. vol. 58, pp. 263-271 (Year: 2012).*
Chen, R-R. et al., Site-specific Mutagenesis of the *Arabidopsis* Gene 5-enolpyruvy-shikimate-3-phosphate Synthase (EPSPS) to Gain Glyphosate-resistant Transgenic *Arabidopsis thaliana*, Journal of Agricultural Biotechnology, 2014, pp. 397-405, 22(4).
Yu, Z. et al., Bioresistance or Biodegradation of Glyphosate and Construction of Transgenic Plants, Molecular Plant Breeding, 2003, pp. 435-441, vol. 1 No. 4.
Zhu Y et al., Bioresistance or Biodegradation of Glyphosate and Construction of Transgenic Plants, Molecular Plant Breeding, 2003, pp. 435-441, vol. 1, No. 4, China Academic Journal Electronic Publishing House.

* cited by examiner

*Primary Examiner* — David H Kruse
(74) *Attorney, Agent, or Firm* — IP & T Group LLP

(57) ABSTRACT

Provided are a glyphosate-resistant gene screening method, an EPSPS mutant gene having glyphosate resistance screened by the method, an EPSPS and C-P Lyase deficient strain and a use thereof.

12 Claims, 3 Drawing Sheets

Specification includes a Sequence Listing.

```
OsE    ATGGCGTCCAACGCCGCGGCTGCGGCGGCGAAGGCGGAGGAGATCGTGCTCCAGCCCATC    60
  1    M  A  S  N  A  A  A  A  A  A  K  E  E  I  V  L  Q  P  I
OsEM   ATGGCGTCCAACGCCGCGGCTGCGGCGGCGAAGGCGGAGGAGATCGTGCTCCAGCCCATC    60
  1    M  A  S  N  A  A  A  A  A  A  K  E  E  I  V  L  Q  P  I

OsE    GTTCACTACATGCTTGAGGCCCTGAAAGCCCTCGGCTCTCTGTGGAAGCAGATAAAGTT    240
 61    V  H  Y  M  L  E  A  L  K  A  L  G  S  V  E  A  D  K  V
OsEM   GTTCACTACATGCTTGAGGCCCTGAAAGGCCTCGGCTCTCTGTGGAAGCAGATAAAGTC    240
 61    V  H  Y  M  L  E  A  L  K  G  L  G  S  V  E  A  D  K  V

OsE    GAGGAAGTGCAACTCTTCTTGGGGAACGCTGCGACTGCAATGCGACTCTGACAGCAGCC    360
101    E  E  V  Q  L  F  L  G  N  A  A  T  A  M  R  L  L  T  A  A
OsEM   GAGGAAGTGCAACTCTTCTTGGGGAACGCTGCGACTGCAATGCGATCCTGACAGCAGCC    360
101    E  E  V  Q  L  F  L  G  N  A  A  T  A  M  R  S  L  T  A  A

OsE    GTGACTGCTGCTGGTGGAAATGCAACTTATGTCCTTGATGGAGTGCCACGAATGAGGGAG    420
121    V  T  A  A  G  N  A  T  Y  V  L  D  G  V  P  R  M  R  E
OsEM   GTGACTGCTGCTGGTGGAAATGCAACTTATGTCCTGATGGAGTGCCACGAATGAGGGAG    420
121    V  T  A  A  G  N  A  T  Y  V  L  D  G  V  P  R  M  R  E

OsE    AGACCGATTGGTGACTTGGTTGTCGGGTTGAAACAACTTGGTGCGGATGTCGACTGTTTC    480
141    R  P  I  G  D  L  V  V  G  L  K  Q  L  G  A  D  V  D  C  F
OsEM   AGACCGATTGGTGACTTGGTTGTCGGGTTGAAGCAACTTGGTGCGGATGTCGACTGTTTC    480
141    R  P  I  G  D  L  V  V  G  L  K  Q  L  G  A  D  V  D  C  F

OsE    TTGGCCCTTGGGGATGTGGAGATCGAAATCATTGACAAACTAATCTCCATTCCTTACGTT    660
201    L  A  L  G  D  V  E  I  E  I  I  D  K  L  I  S  I  P  Y  V
OsEM   TTGGCGCTTGGGGATGTGGAGATCGAAATCATTGACAAACTAATCTCCATTCCTTACGTT    660
201    L  A  L  G  D  V  E  I  E  I  I  D  K  L  I  S  I  P  Y  V

OsE    GGTGATGCCTCAAGCGCGAGCTATTTCTTGGCTGGTGCTGCAATCACTGGAGGCACTGTG    840
261    G  D  A  S  S  A  S  Y  F  L  A  G  A  A  I  T  G  G  T  V
OsEM   GGTGATGCCTCAAGCGCGAGCTATTTCTTGGCTGGTGCTGCAATCACTGGGGGCACTGTG    840
261    G  D  A  S  S  A  S  Y  F  L  A  G  A  A  I  T  G  G  T  V

OsE    TTCCCCAACTACTTCGACGTTCTAAGCACTTTCGTCAGGAACTG                  1364
441    F  P  N  Y  F  D  V  L  S  T  F  V  R  N  *
OsEM   TTCCCCAACTACTTCGACGTTCTAAGCACTTTCGTCAGGAACTG                  1364
441    F  P  N  Y  F  D  V  L  S  T  F  V  R  N  *
```

Figure 3

```
GmE   ATGGATAGCGTGGCGGCGGCGGAAAAACCGAGCACCAGCCCGGAATTGTGCTGGAACCG       60
  1    M  D  S  V  A  A  A  E  K  P  S  T  S  P  E  I  V  L  E  P
GmEM  ATGGATGAGCGTGGCGGCGGCGGAAAAACCGAGCACCAGCCCGGAATTGTGCTGGAACCG      60
  1    M  D  E  R  G  G  G  K  T  E  H  Q  P  G  I  V  L  E  P

GmE   CCGCTGGCGCTGGGCGATGTGGAAATTGAAATTGTGGATAAACTGATTAGCGTGCCGTAT      660
 201   P  L  A  L  G  D  V  E  I  E  I  V  D  K  L  I  S  V  P  Y
GmEM  CCGCTGGCGCTGGGCGATGTGGAAATTTATATTGTGGATAAACTGATTAGCGTGCCGTAT      660
 201   P  L  A  L  G  D  V  E  I  Y  I  V  D  K  L  I  S  V  P  Y

GmE   CGCGATGTGGCGAGCTGGCGCGTGAAAGAAACCGAACGCATGATTGCGATTTGCACCGAA    1140
 361   R  D  V  A  S  W  R  V  K  E  T  E  R  M  I  A  I  C  T  E
GmEM  CGCGATGTGGCGAGCTGGCGCGTGAAAGAGACCGAACGCATGATCGCGATTTGCACCGAA    1140
 361   R  D  V  A  S  W  R  V  K  E  T  E  R  M  I  A  I  C  T  E

GmE   ACCTTTCCGGATTATTTTGAAGTGCTGGAACGCCTGACCAAACATTA                 1387
 441   T  F  P  D  Y  F  E  V  L  E  R  L  T  K  H  *
GmEM  ACCTTTCCGGATTATTTTGAAGTGCTGGAACGCCTGACCAAACATTA                 1387
 441   T  F  P  D  Y  F  E  V  L  E  R  L  T  K  H  *
```

Figure 4

GLYPHOSATE-RESISTANT GENE SCREENING METHOD, EPSPS MUTANT GENE AND DEFICIENT STRAIN AND USE

CROSS-REFERENCE TO RELATED APPLICATIONS

The present application is a continuation-in-part application based on international patent application No. PCT/CN2016/082409, filed on May 17, 2016 and entitled "Glyphosate-Resistant Gene Screening Method, EPSPS Mutant Gene And Deficient Strain And Use", which is incorporated herein by reference in its entirety.

TECHNICAL FIELD

The present disclosure relates to the technical field of biology, and specifically to a method for screening a glyphosate-resistant gene, an EPSPS mutant gene and a knock-out strain, and uses thereof.

BACKGROUND ART

Glyphosate, developed by Monsanto Company USA, is a Broad-spectrum, non-selective systematic herbicide which is applied via foliar spray. It works by inhibiting the activity of 5-enolpyruvylshikimate-3-phosphate synthase (EPSPS) in the shikimate pathway in a plant so as to keep the affected plant from continuing to synthesize essential amino acids and thus affect the normal growth of the plant, eventually lead to death.

Glyphosate is a broad-spectrum glyphosate-based herbicide which is lethal to almost all kinds of plants. The most commonly used glyphosate-resistant gene on the market is CP4 gene which is a highly glyphosate-resistant gene that is separated from *Agrobacterium* by Monsanto. Plants may obtain such resistance by means of gene transformation. Since glyphosate-resistant crops bring obvious benefits to agriculture and environment, transgenic corn and soybean varieties containing CP4 gene have been massively popular over the last 20 years. However, there is still a constant demand for new glyphosate-resistant genes and crop varieties with these new genes.

In creating a non-transgenic glyphosate-resistant plant by gene editing technology, it is preferable that it has glyphosate-resistant plant EPSPS gene. Microorganism EPSPS genes, typically CP4, provide glyphosate resistance. However, even if such microorganism EPSPS genes are transferred to a plant by gene editing method, such plant would likely be still seen as a transgenic plant as such genes come from a different species and can hardly be accepted by the general public. The public are biased against transgenic crops here, which hinders the development and commercialization of transgenic technology. Therefore, it is a key to create highly glyphosate-resistant plant EPSPS gene for obtaining non-transgenic glyphosate-resistant crops.

Theoretically, plants can be mutated by chemical and/or radiation treatment and glyphosate-resistant plants obtained by screening the mutated plants under a certain glyphosate stress. As a matter of fact, over years of glyphosate application in large amounts, some weeds have evolved to be resistant to glyphosate, as a result of changes of EPSPS gene in most of the cases. But such changes most occur as increase in gene copy number and the resistance as a result of such changes is not high, so such changes can hardly be used in crops. There are some crops of which themselves the EPSPS gene mutates to be resistant to glyphosate, but such resistance is not as good as CP4. To create highly glyphosate-resistant non-transgenic crops, we have to keep mutating and screening crops or other plants for EPSPS gene resistant genes.

However, the existing methods of screening for glyphosate-resistant mutant genes from crops or other plants comprise first subjecting plants to mutagenesis to obtain a number of mutant plants, and then performing screening of such mutant plants for resistance to obtain glyphosate-resistant mutant plants, and then testing and analyzing the genomes of the resistant plants to finally obtain glyphosate-resistant mutant genes. Due to a long period of plant growth, it not only takes a long time to grow a large number of mutant plants, but also requires a massive acreage.

SUMMARY

A purpose of the present disclosure is to provide a method for screening glyphosate-resistant mutant genes. By this method, it is possible to quickly obtain mutant gene from a plant by screening. Mutant genes obtained by screening according to this screening method are resistant to glyphosate.

Another purpose of the present disclosure is to provide a mutant gene. The mutant gene is obtained by screening according to the above screening method and it is resistant to glyphosate.

A further purpose of the present disclosure is to provide a use of the above mutant gene in a way that the plant transformed with the mutant gene would be resistant to glyphosate.

A still further purpose of the present disclosure is to provide a model strain for screening glyphosate-resistant mutant genes. Such model strain cannot express EPSPS or lyse glyphosate.

A still further purpose of the present disclosure is to provide a use of the above model strain in testing functions of plant-derived EPSPS genes.

A still further purpose of the present disclosure is to provide a use of the above model strain in testing the glyphosate resistance of plant-derived EPSPS genes.

A still further purpose of the present disclosure is to provide a use of the above model strain in testing the glyphosate resistance of plant-derived mutant EPSPS genes.

The present disclosure solves technical problems by using the following technical solutions:

A method for screening glyphosate-resistant genes, including:

knocking out interference genes of a source strain by a gene knockout technology to obtain a knock-out strain, wherein the source strain is one of *Escherichia coli* DH5α, TOP10 and BL21, the interference genes include EPSPS gene and C-P lyase genes, and the knock-out strain is an EPSPS gene-and-C-P lyase genes-deleted strain;

first introducing an exogenous EPSPS gene into the knock-out strain which is then subjected to mutagenesis treatment, so as to obtain first mutant strains containing exogenous EPSPS mutant genes, wherein the exogenous EPSPS gene come from a target plant;

or, first mutating the exogenous EPSPS gene to obtain exogenous EPSPS mutant genes, and then introducing the exogenous EPSPS mutant genes into the knock-out strain to obtain second mutant strains;

placing the first mutant strains or the second mutant strains on screening culture media containing glyphosate, culturing for screening, so as to obtain monoclonal resistant strains having resistance to glyphosate; and sequencing and verifying the monoclonal resistant strains, so as to obtain EPSPS mutant genes resistant to glyphosate.

The method for screening glyphosate-resistant genes, EPSPS mutant genes and knock-out strains and use thereof provided by the present disclosure provide the following beneficial effects. Compared with the existing screening methods of screening glyphosate-resistant mutant genes from plants, the screening method provided by the present disclosure comprises constructing EPSPS gene-and-C-P lyase genes-deleted strains, introducing exogenous EPSPS genes from a target plant into the EPSPS gene-and-C-P lyase genes-deleted strains which are used as host strains, so as to obtain mutant strains containing exogenous EPSPS mutant genes, i.e. an exogenous EPSPS gene mutant library, and then screening glyphosate-resistant EPSPS mutant genes from the exogenous EPSPS gene mutant library. Utilizing the fast reproduction speed and small size of bacteria, the screening method of the present disclosure overcomes the problems of long period and large acreage of the current plant screening methods. The screening method of the present disclosure is characterized by short period, extremely small space and simple operation, in directed screening of glyphosate-resistant EPSPS genes. Furthermore, using EPSPS gene-and-C-P lyase genes-deleted strain as the host strain, the screening method provided of the present disclosure effectively avoids the situation where glyphosate resistance is developed as a result of mutation of the EPSPS gene and C-P lyase genes of the host strains themselves. Therefore, the screening results are more scientific and reliable.

BRIEF DESCRIPTION OF DRAWINGS

In order to more clearly illustrate the technical solutions provided in the embodiments of the present disclosure, drawings necessary for the embodiments are briefly described below. It should be understood that the following drawings merely show some embodiments of the disclosure and thus should not be construed as limiting the scope. Other related drawings can be obtained by those ordinarily skilled in the art according to these drawings without paying any creative effort.

FIG. 3 shows the result of comparative analysis between the sequences of *Oryza sativa* EPSPS mutant gene (SEQ. ID. NO. 4) and wild type *Oryza sativa* EPSPS gene (SEQ. ID. NO. 1) according to Example 1 of the present disclosure; and FIG. 4 shows the result of comparative analysis between the sequences of *Glycine max* EPSPS mutant gene (SEQ. ID. NO, 10) and wild type *Glycine max* EPSPS gene (SEQ. ID. NO. 5) according to Example 2 of the present disclosure.

DETAILED DESCRIPTION OF EMBODIMENTS

Figure 1:
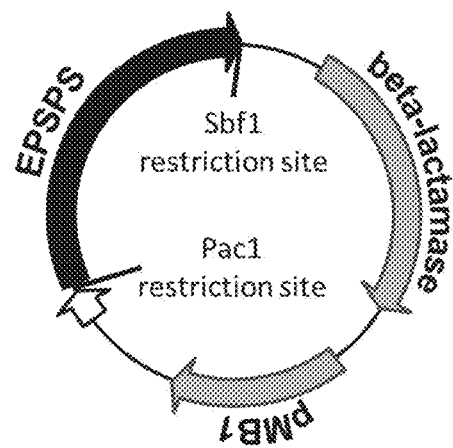
FIG. 1 is a structural diagram of pADV5 vector according to an example of the present disclosure.

To make the purposes, technical solutions and advantages of the present disclosure more clear, the technical solutions in the examples of the present disclosure will be clearly and completely described below. Examples for which no specific condition is indicated should be done under conventional conditions or conditions as recommended by the manufacturer. All those agents or instruments for which no manufacturer is indicated are all conventional products which are commercially available.

Now provided is a detailed description of the method for screening glyphosate-resistant genes, EPSPS mutant gene and knock-out strain and use thereof of the present disclosure.

A method for screening glyphosate-resistant gene, including followings.

Step S1: Construction of a Knock-Out Strain

Interference genes of a source strain are knocked out by a gene knockout technology to give a knock-out strain. The source strain is one of *E. coli* DH5α, TOP10 and BL21. The interference genes comprise EPSPS gene and C-P lyase genes. The knock-out strain is an EPSPS gene-and-C-P lyase genes-deleted strain.

That is to say, the EPSPS gene-and-C-P lyase genes-deleted strain is a knock-out strain obtained by knocking out the EPSPS gene and the C-P lyase genes of one of *E. coli* DH5α, TOP10 and BL21. Such EPSPS gene-and-C-P lyase genes-deleted strain is characterized in that it cannot grow on a basal culture medium free of amino acid or protein, also known as limiting culture medium, but can grow on a basal culture medium that contains only glucose as organic source after an exogenous EPSPS gene is introduced.

The functions of the knocking-out of source strain, i.e. knocking-out of EPSPS gene and C-P lyase genes from wild type *E. coli*, are described below.

The endogenous EPSPS gene of *E. coli* can express 5-enolpyruvylshikimate-3-phosphate synthase (EPSPS) and C-P lyase genes can express C-P lyase that lyses C-P bond and thus could lyse glyphosate. Therefore, if wild type *E. coli* is used as a host strain, in the subsequent step of mutagenesis treatment, mutation may also occur in the endogenous EPSPS gene and C-P lyase genes of the host strain, producing endogenous EPSPS mutant gene resistant to glyphosate and C-P lyase mutant gene with improved lysis ability, and providing the host strain with resistance to glyphosate. This makes it impossible to tell whether the glyphosate resistance of the monoclonal resistant strain obtained by screening is to provided by the exogenous EPSP mutant gene or by their endogenous EPSPS mutant gene and C-P lyase mutant gene. Therefore, if *E. coli* is used as a host strain, its endogenous EPSPS gene and C-P lyase genes have to be knocked-out, so as to ensure that the finally obtained glyphosate resistance of the monoclonal resistant strain comes from the exogenous EPSPS mutant gene and that the screening result would be more scientific, reasonable and reliable.

Sure, there are various gene knockout technologies to knock out the EPSPS gene and C-P lyase genes in *E. coli*, e.g. FRT method, pCas system, pKD46 system or direct knockout using homologous PCR fragment. Where the genomic sequence information of *E. coli* is known, it is relatively easy to knock out the EPSPS gene and the C-P lyase genes on its genome using any of the above methods.

Step S2: Construction of Exogenous EPSPS Gene Mutant Library

One construction strategy is to first introduce, using a knock-out strain as a host strain, an exogenous EPSPS gene into the knock-out strain which is then subjected to mutagenesis treatment, so as to obtain first mutant strain containing an exogenous EPSPS mutant gene. Preferably, the mutagenesis treatment is chemical mutagenesis treatment or radiation-induced mutagenesis treatment. Chemical mutagenesis treatment uses chemical mutagens e.g. EMS or DES to induce mutation in the first mutant strain so that mutation occurs in the exogenous EPSPS gene along with the proliferation of the host strain.

Another construction strategy is to first mutate the exogenous EPSPS gene to obtain an exogenous EPSPS mutant gene, and then introduce the exogenous EPSPS mutant gene into a knock-out strain to obtain second mutant strain. Mutagenesis treatment is done by PCR based on mismatch PCR method or DNA Shuffling method using exogenous EPSPS gene as a template, and the resulted PCR product is exogenous EPSPS mutant gene.

It is to be noted that both the first mutant strain and the second mutant strain contain exogenous EPSPS mutant genes, and both the first mutant strain and the second mutant strain are exogenous EPSPS gene mutant libraries.

Terms like "first" and "second" are merely used for purpose of discriminative description, but should not be construed as indicating or implying relative importance.

The exogenous EPSPS gene used in the above step comes from a target plant which is rice, soybean, wheat, corn, barley, sorghum, tobacco, cotton, sweet potato, poplar, potato, Chinese cabbage, cabbage or green pepper. One may choose as actually required in an actual screening process.

Step S3: Resistance Screening

The exogenous EPSPS gene mutant library, i.e. the first mutant strain or the second mutant strain, obtained from Step S2 is placed on screening culture media containing glyphosate, followed by culturing for screening, so as to obtain a monoclonal resistant strain having resistance to glyphosate. It is to be noted that the monoclonal resistant strain, i.e. the colonies growing on the screening culture media, may also be called as positive transformant. Sure, there may be various numbers of positive transformants, for example, there may be one positive transformant or a plurality of positive transformants.

The screening culture media are M9 basal culture media containing different concentrations of glyphosate.

Step S4: Sequencing and Verification

The monoclonal resistant strain obtained from Step S3 are sequenced and verified, so as to obtain EPSPS mutant genes resistant to glyphosate.

Now the characteristics and effects of the present disclosure will be further described in details with reference to examples.

Example 1

The screening method provided by the present disclosure is further described in details in the present example wherein *Oryza sativa* was used as the target plant, the exogenous EPSPS gene was *Oryza sativa* EPSPS gene (see SEQ ID NO.1 for its nucleotide sequence), and an EPSPS gene-and-C-P lyase genes-deleted strain obtained by knocking out the EPSPS gene and C-P lyase genes in wild type *E. coli* DH5α using homologous PCR fragments was adopted as a host strain. See Table 1 for the names and their nucleotide sequences of primers used in the present example.

Step 1, is to directly knock out the EPSPS gene and C-P lyase genes in *E. coli* DH5α using homologous PCR fragments.

1. Knocking Out the C-P Lyase Genes in *E. coli* DH5α
(1) Amplification of Homologous PCR Fragment Forward primer CPF2 and reverse primer CP5HA3 (see Table 1) were used to conduct PCR with wild type *E. coli* DH5α being used as a template. The gel was used to purify the PCR product, named as CP5HA fragment, with a length of 525 bp. See SEQ ID NO.13 for its nucleotide sequence.

TABLE 1

Primers and their nucleotide sequences used in the present example

| Primer name | Nucleotide sequence (5'-3') | SEQ ID NO |
|---|---|---|
| CPF2 | agctgtaacaggcgttcagcctcc | 23 |
| CP5HA3 | gcagatgtacatgccgttatcttc | 24 |
| CP3HA5 | ggacgcatgttacgtctcaccgg | 25 |
| CPR2 | aatacgccgttcgagacgcatctc | 26 |
| SPE35 | gcccagtatcagcccgtcatacttg | 27 |
| CPR0 | ctcatgccgaataccagcccgtag | 28 |
| SPEC5 | ctccgaatacacttacgaagataacggcatgtacatct gctaatacgactcactatagggagaatg | 29 |
| SPEC3 | cttcggcaatgcccgcgccggtgagacgtaacatgcgt ccttatttgccgactaccttggtg | 30 |
| EE5-1K | tagttctggtccggcaatgctacc | 31 |
| ES5HA3 | gcagattaatagtgccatcgacacg | 32 |
| ES3HA5 | cggattagccaggcagcctgaatg | 33 |
| EE3-1K | gcttgggccatcaatggtaataacc | 34 |
| GM5L | ctgacgttacaacccatcgctcgtgtcgatggcactatt aatctgcagaggcggtttgcgtattgggcgc | 35 |
| GM3L | gctatttattgcccgttgttcattcaggctgcctggcta atccgtgatctcggcttgaacgaattgttag | 36 |
| ECES35U | tgattatatttcctgcacgcgtggt | 37 |
| PV325 | tgagcgcaacgcaattaatgtgag | 38 |
| PV323 | cgtaaggagaaaataccgcatcagg | 39 |
| 2M1H | ttacgtacgttaattaatggcgtccaacgccgcggctgcg | 40 |
| 2M1T | ttacgtacgtcctgcaggtcagttcctgacgaaagtgctt agaacg | 41 |

Forward primer CP3HA5 and reverse primer CPR2 were used to conduct PCR with *E. coli* DH5α being used as a template. The gel was used to purify the PCR product, named as CP3HA fragment, with a length of 503 bp. See SEQ ID NO.14 for its nucleotide sequence.

Forward primer SPEC5 and reverse primer SPEC3 were used to conduct PCR with a vector named pCPSG7 containing the nucleotide sequence as shown in SEQ ID NO.2 being used as a template. The gel was used to purify the PCR product, named as SPEC fragment, with a length of 900 bp. See SEQ ID NO.15 for its nucleotide sequence.

CPF2 and CPR2, as primers, were used to conduct PCR with CP5HA fragment, SPEC fragment and CP3HA fragment being used as templates (conducted in the same reaction system). The gel purified PCR product was named as CP5HA-SPEC-CP3HA fragment, with a length of 1849 bp. See SEQ ID NO.16 for its nucleotide sequence. Located on site 1 to site 525 were 5 terminal of *E. coli* PhnA gene and its upstream sequence. The nucleotide sequence from site 526 to site 1346 consisted of Spectinomycin resistant gene and its promoter. Located on site 1347 to site 1849 were 3 terminal of *E. coli* PhnH gene and its downstream sequence.

(2) Transformation by Heat Shock

*E. coli* DH5α competent cells were prepared by a conventional method. 100 μL of *E. coli* DH5α competent cells were gently blended with 5 μL of CP5HA-SPEC-CP3HA fragment. Then they were left on ice for 10 min, heat-shocked for 90 s at 42° C. and then immediately transferred to ice and standing for 2 min.

Then they were quickly added to 1 mL of LB liquid culture medium (containing 50 μg/mL of Spec (spectinomycin)), cultured at 37° C. for 1 hr, then spread on an plate of LB solid culture medium (containing 50 μg/mL of Spec) and then cultured overnight at 37° C.

After the cultured E. coli DH5α was tested with forward primer SPE35 and reverse primer CPR0, the strain was named as EDC, which is E. coli DH5α with C-P lyase genes being knocked out.

2. Knocking Out the EPSPS Genes in EDC (E. coli DH5α with C-P Lyase Genes being Knocked Out)

(1) Amplification of Homologous PCR Fragment

Forward primer EE5-1K and reverse primer ES5HA3 were used to conduct PCR with wild type E. coli DH5α being used as a template. The gel purified PCR product was named as ES5HA fragment, with a length of 1194 bp. See SEQ ID NO.17 for its nucleotide sequence.

Forward primer ES3HA5 and reverse primer EE3-1K were used to conduct PCR with E. coli DH5α being used as a template. The gel purified PCR product was named as ES3HA fragment, with a length of 1168 bp. See SEQ ID NO.18 for its nucleotide sequence.

Forward primer GM5L and reverse primer GM3L were used to conduct PCR with a vector named pCPSG5 containing the nucleotide sequence as shown in SEQ ID NO.3 being used as a template. The gel purified PCR product was named as GM fragment, with a length of 1050 bp. See SEQ ID NO.19 for its nucleotide sequence.

Forward primer EE5-1K and reverse primer EE3-1K were used to conduct PCR with the ES5HA fragment, GM fragment and ES3HA fragment being used as templates. The gel purified PCR product was named as ES5HA-GM-ES3HA fragment, with a length of 3322 bp. See SEQ ID NO.20 for its nucleotide sequence. Located on site 1 to site 1194 was the upstream sequence of E. coli EPSPS gene. The nucleotide sequence from site 1195 to site 2154 consisted of gentamicin resistant gene and its promoter. Located on site 2155 to site 3322 was the downstream sequence of E. coli EPSPS gene.

(2) Transformation by Heat Shock

EDC competent cells were prepared with a conventional method. 100 μL of EDC competent cells were gently blended with 5 μL of ES5HA-GM-ES3HA fragment. Then they were left on ice for 10 min, heat-shocked at 42° C. for 90 s and then immediately transferred to ice and standing for 2 min. Then they were quickly added to 1 mL of LB liquid culture medium, cultured at 37° C. for 1 hr, spread on a plate of LB solid culture medium containing Spec (50 μg/mL) and Gm (50 μg/ml) (containing 50 μg/ml of Spec and 50 μg/ml of Gm) and then cultured overnight at 37° C.

The cultured strain was tested with forward primers EE5-1K and GM3L and reverse primers EE3-1K and ECES35U and was named as EDCE, which was E. coli DH5α with its EPSPS gene and C-P lyase genes being knocked out, i.e. an EPSPS gene-and-C-P lyase genes-deleted strain.

Sure, other conventional knock-in or knock-out methods may also be used. E.g., pCas system is used to knock out the EPSPS gene and C-P lyase genes in E. coli DH5α or pKD46 system is used to knock out the EPSPS gene and C-P lyase genes in E. coli DH5α.

Step 2, is to, using the EPSPS gene-and-C-P lyase genes-deleted strain obtained in step 1 as a host strain, introduce EPSPS gene from Oryza sativa into the host strain, so as to obtain mutant strain, i.e. Oryza sativa EPSPS gene mutant library. Specifically, the operation is described below.

1. Constructing an EPSP Gene Mutant Library with Mismatch PCR Method

The mRNA of Oryza sativa EPSPS gene was reverse transcribed into cDNA by a conventional method and the cDNA was cloned to pADV5 vector (see FIG. 1 for its structure).

Forward primer PV325 and reverse primer PV323 were used to conduct a first round of mismatch PCR with pADV5 vector carrying Oryza sativa EPSPS gene being used as a template. The PCR reaction system comprises 25.3 μL of $H_2O$, 4 μL or error-prone PCR MIX, 4 μL of error-prone PCR dNTP, 4 μL of $MnCl_2$, 0.8 μL of PV325, 0.8 μL of PV323, 0.1 μL of Taq enzyme and 2 μL of template. The PCR reaction was conducted in the following procedure: 95° C. for 30 s; 60° C. for 30 s; 72° C. for 2 min. After 40 cycles, the PCR product was subjected to electrophoresis with 1% agarose. Then the gel was cut and recovered. The first round PCR product was obtained.

Forward primer 2M1H and reverse primer 2M1T were used to conduct a second round of PCR with the first round PCR product being used as a template. The PCR system consisted of 31.9 μL of $H_2O$, 2.5 μL of DMSO, 5 μL of 10×PCR buffer, 5 μL of dNTP, 4 μL of $MgCl_2$, 0.5 μL of 2M1H, 0.5 μL of 2M1T, 0.1 μL of Taq enzyme and 0.5 μL of template. The PCR reaction was conducted in the following procedure: 95° C. for 30 s; 60° C. for 30 s; 72° C. for 2 min; 60 cycles.

The resulted PCR product was subjected to electrophoresis with 1% agarose and those bands having a size identical to the target band (1.5 kb) were subjected to gel recovery and purification. The purified product was digested by double enzymes, i.e. PacI and SbfI, and then ligated to a new pADV5 vector which was also digested by the double enzymes, so as to give a ligation product. The ligation product obtained in this step was pADV5 vector carrying Oryza sativa EPSPS mutant gene.

Sure, also, DNA Shuffling method may be used to obtain pADV5 vector carrying Oryza sativa EPSPS mutant gene. Specifically, the operation is described below.

pADV5 vectors carrying gene mutants of Oryza sativa EPSPS gene was obtained by DNA Shuffling method. 1) PCR amplification was conducted on Oryza sativa EPSPS gene sequence, the amplification product was subjected to electrophoresis with 1% agarose, and then gel recovery and purification were conducted; 2) the recovered product was digested by DNase enzyme, and then subjected to electrophoresis with 1.2% agarose after digestion, fragments with a size of 100 bp, 200 bp or 300 bp were cut off for gel recovery and purification; 3) a first round of PCR of gene shuffling was conducted using 3 μL of the gel recovery product from step 2) as a template, without any primer in this round of PCR, and then 60 cycles of amplification were done; 4) 10 μL of PCR products from step 3) were subjected to electrophoresis to see if there were big fragments with a continuous range. If it was as expected, the remaining PCR products were used as templates for the next round of PCR; 5) 0.5 μL of PCR products from step 3) were used as the template for the next round of PCR, in which primers designed to have enzyme cutting sites were used as PCR primers, and 60 cycles of amplification were done; 6) the PCR products from step 5) was subjected to electrophoresis with 1% agarose gel, single bands bigger than 500 bp were cut off for gel recovery and purification; 7) double enzyme digestion was conducted on the gel recovery products from step 6) using restriction endonucleases, electrophoresis was conducted with 1% agarose gel after double enzyme digestion, the target fragments were cut off and frozen with liquid nitrogen and the gel was removed, then they were ligated with pADV5 vectors which were also subjected to the same double enzyme digestion. Thus, a plurality of pADV5 vectors carrying gene mutants of Oryza sativa EPSPS gene were obtained.

(2) Transforming EDCE (E. coli DH5α with EPSPS Gene and C-P Lyase Genes being Knocked Out)

EDCE competent cells were prepared with a conventional method. The above ligation product (pADV5 vectors carrying Oryza sativa EPSPS mutant gene) was added to 50 μL EDCE competent cells. They were fully mixed and left on ice for 30 min, then heat-shocked at 42° C. for 90 s, and left in ice bath for 2 min. Then they were added to 500 μL of LB liquid culture medium and cultured under shaking at a low speed (150 r/min) at 37° C. for 90 min.

pADV5 vectors carrying Oryza sativa EPSPS mutant gene were transformed into EDCE to give mutant strain, i.e. Oryza sativa EPSPS gene mutant library. The Oryza sativa EPSPS gene mutant library contains numerous Oryza sativa EPSPS mutant genes. Every single mutant strain is equivalent to an Oryza sativa EPSPS gene mutant plant. Therefore, when used to screen the same order of magnitude of Oryza sativa EPSPS mutant genes, compared with the existing screening methods, the present screening method skips the culture period of Oryza sativa and saves the acreage to be occupied, with much less time and high efficiency, and convenient and easy operations, especially, requiring a very small space and enabling screening just on culture media.

Step 3, is to inoculate the above mutant strain on screening culture media for resistance screening.

A plurality of the above obtained mutant strains were inoculated on a plurality of screening culture media with different concentrations of glyphosate, respectively (the screening culture media contained different concentrations of glyphosate, and the glyphosate concentrations contained in them were 10 mM, 20 mM, 50 mM, etc., respectively, having a gradient in glyphosate concentrations, and of course, the glyphosate concentration may be set as required), and cultured at 37° C. overnight. The screening culture media were obtained by using M9 as a basal medium, to which certain concentrations of antibiotics, including Specs (Spectinomycin), Gen (Gentamycin) and Amp (Ampicillin), and different concentrations of glyphosate were added. M9 culture medium consists of the following ingredients: 13~14 g/L of $Na_2HPO_4$, 5.7~6.3 g/L of $KH_2PO_4$, 0.9~1.1 g/L of NaCl, 1.8~2.2 g/L of $NH_4Cl$, 37~43 g/L of glucose, 48~52 g/L of $MgSO_4.7H_2O$ and 21~23 g/L of $CaCl_2$.

Step 4, is sequencing and verification.

Monoclonal resistant strains growing on the screening culture media were selected and separated so as to check for their glyphosate resistance, and they were sequenced and verified, giving glyphosate-resistant Oryza sativa EPSPS mutant gene sequences. One of the Oryza sativa EPSPS mutant genes is taken as an example for explanation. As can be seen in SEQ ID NO.4, its nucleotide sequence consists of 1365 bases. This *Oryza sativa* EPSPS mutant gene (which was named as OsEM gene) was compared with wild type *Oryza sativa* EPSPS gene (which was named as OsE gene) in terms of their nucleotide sequences (as shown in SEQ ID NO.1) and the amino acid sequences they coded. FIG. 3 shows the result. In the *Oryza sativa* EPSPS mutant gene, in a direction from 5' terminal to 3' terminal, the base on site 209 mutates from "C" to "G", the base on site 240 mutates from "T" to "C", two consecutive bases on site 346 and site 347, mutate from "CT" to "TC", the base on site 396 mutates from "T" to "C", the base on site 453 mutates from "A" to "G", the base on site 606 mutates from "C" to "T", and the base on site 831 mutates from "A" to "G". Only the base on site 209 mutates from "C" to "G", causing site 70 (from the amino terminal to the carboxyl terminal) in the amino acid residue sequence it codes to mutate from alanine residue to glycine residue. And two consecutive bases on site 346 and site 347 mutate from "CT" to "TC", causing site 116 in the amino acid residue sequence it codes to mutate from leucine residue to serine residue. The remaining mutation of bases does not cause changes of amino acid residues they code.

For glyphosate resistance testing of *Oryza sativa* EPSPS mutant gene, *E. coli* (EPSPS gene-and-C-P lyase genes-deleted strain) respectively transformed with OsEM gene (experimental group) and OsE gene (control group) were inoculated to culture media containing 0 mM, 1 mM, 5 mM, 10 mM, 20 mM, 50 mM and 100 mM glyphosate to see the growth of *E. coli* (indicated by growth saturation index: saturation index=0, no growth; saturation index=1, minor growth; saturation index=2, growth to half-saturation; saturation index=3, vigorous growth, but still not saturated; saturation index=4, rapid growth, meaning the strains have reached the maximum (saturation) concentration or the growth has reached the limit). Table 2 shows the result.

TABLE 2

Growth saturation index of *E. coli* transformed with OsEM gene and OsE gene in culture media with different concentrations of glyphosate

| Gene | Growth saturation index 0 mM | 1 mM | 5 mM | 10 mM | 20 mM | 50 mM | 100 mM |
|---|---|---|---|---|---|---|---|
| OsE | 4 | 0 | 0 | 0 | 0 | 0 | 0 |
| OsEM | 4 | 4 | 4 | 4 | 4 | 4 | 0 |

As can be seen from Table 2, both the experimental group (containing OsEM gene) and the control group (containing OsE gene) show normal growth (the saturation index of both being 4) on the culture medium containing 0 mM glyphosate; on culture media containing 1 mM, 5 mM, 10 mM, 20 mM and 50 mM glyphosate, the strains of control group cannot grow (the saturation index being 0), whereas the experimental group shows normal growth (the saturation index being 4); on the culture medium containing 100 mM glyphosate, neither the experimental group nor the control group shows normal growth (the saturation index being 0). This indicates that the *Oryza sativa* EPSPS mutant gene (see SEQ ID NO.4 for its nucleotide sequence) screened in the present example can provide EPSPS gene-and-C-P lyase genes-deleted *E. coli* with glyphosate resistance so that the *E. coli* can grow on a culture medium containing up to 50 mM glyphosate.

The glyphosate-resistant mutant gene, e.g. *Oryza sativa* EPSPS mutant gene, obtained by screening with the method for screening glyphosate-resistant gene provided by the present example of the present disclosure is resistant to 50 mM glyphosate. See SEQ ID NO.4 for its nucleotide sequence.

Directly using the glyphosate-resistant mutant gene, e.g. *Oryza sativa* EPSPS mutant gene, (see SEQ ID NO.4 for its nucleotide sequence) obtained by screening by the method for screening glyphosate-resistant gene provided by the present example of the present disclosure to transform rice or soybean or other plants provides the transformed plants with glyphosate resistance. Sure, transformation methods commonly used in the field of gene engineering may be used, e.g. *Agrobacterium*-mediated method, gene gun-mediated transformation, protoplast-mediated method, or electroporation, to transform rice or soybean or other plants so that the transformed plants get resistance to glyphosate.

Example 2

The screening method provided by the present disclosure is described in the present example wherein *Glycine max* was used as the target plant, the exogenous gene was *Glycine max* EPSPS gene (see SEQ ID NO.5 for its nucleotide sequence), an EPSPS gene-and-C-P lyase genes-deleted strain obtained by directly knocking out the EPSPS gene and C-P lyase genes in wild *E. coli* DH5α using homologous FRT method was used as a host strain. See Table 3 for the names of primers used in the present example and their nucleotide sequences.

Step 1, is to knock out the C-P lyase genes of the *E. coli* DH5α.

The EPSPS gene and C-P lyase genes in *E. coli* DH5α strain were knocked out using FRT method. The knock-out was carried out in two steps. The C-P lyase genes was knocked out first, and then the EPSPS gene was knocked out.

Figure 2:
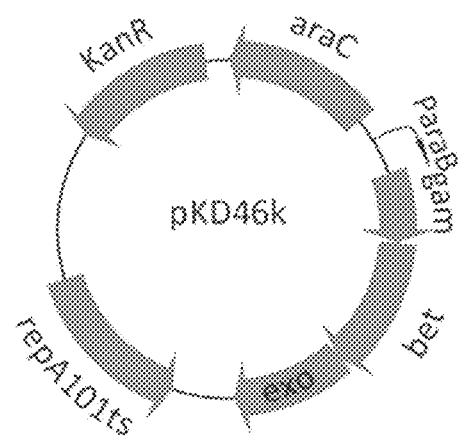
FIG. 2 is a structural diagram of pKD46 vector according to an example of the present disclosure.

1. Preparation of *E. coli* DH5α Competent Cells Containing pKD46 Plasmid 0.5 μL of pKD46 plasmid (see FIG. 2 for its structure) was used to transform *E. coli* DH5α competent cells. Positive colonies were screened on an LB culture medium plate (containing Amp 00).

Positive monoclonal colonies were selected to be inoculated in small amount of M9-sucrose liquid culture medium (containing sucrose), and cultured overnight at shaking speed of 180 rpm and temperature of 30° C.

After culturing, they were inoculated in larger amount of M9-sucrose liquid culture medium (containing sucrose+100 μg/mL Amp+10 mM L-arabinose) at a ratio of 1:10, and cultured at 30° C. until OD600 of the culture reaches about 0.7.

The above strain culture was cooled on ice for 20 min. The microbial cells were recovered by centrifuging at 4° C. and 4000 rpm, resuspended with 40 mL of pre-cooled 10% (v/v) glycerol, and repeatedly washed for 3 times. The supernatant was discarded. Then the residues were resuspended with 400 μL of pre-cooled 10% glycerol and divided and packed by 100 μL/tube, thus giving DH5α resistant to Amp.

2. Knocking Out the C-P Lyase Genes in *E. coli* DH5α

Forward primer C-P lyase_P15 and reverse primer C-P lyase_P13 (see Table 3) were used to conduct PCR amplification with *E. coli* DH5α genome being used as a template. P1 fragment was obtained. See SEQ ID NO.6 for the nucleotide sequence of P1 fragment.

Forward primer C-P lyase_P25 and reverse primer C-P lyase_P23 were used to conduct PCR amplification with *E. coli* DH5α genome being used as a template. P2 fragment was obtained. See SEQ ID NO.7 for the nucleotide sequence of P2 fragment.

P1 and P2 were purified through 1% agarose electrophoresis. Thereby, purified PCR products were obtained. They were added to plasmid containing Gen resistant fragments in proportion to make a mixing pool which was used as a template for PCR amplification using forward primer C-P lyase_P15 and reverse primer C-P lyase_P23. Thereby, PRC fragment with a length of 1586 bp was obtained. See SEQ ID NO.21 for its nucleotide sequence.

50 μL of *E. coli* DH5α competent cells (Amp-resistant DH5α) were gently mixed with 30 μL of purified PRC fragments. Then they were placed in a 0.1 cm pre-cooled electroporation cuvette and subjected to electroporation by Bio-Rad electroporator at 1.8 kV.

They were quickly added to 1 mL of M9-sucrose liquid culture medium containing 10 mM of arabinose, cultured at 30° C. for 1 h and then spread on a plate of LB solid culture medium (containing 100 μg/mL of Amp and 30 μg/mL of Gen) so as to screen recombinant strains resistant to both Amp and Gen, which were then cultured at 30° C. overnight.

After the culture, forward primer C-P lyase_5UTR and reverse primer C-P lyase_Gen3 were used to screen positive clones containing Gen gene to prove the presence of Gen gene.

The positive clones were inoculated on an LB+Amp liquid culture medium and cultured at 30° C. overnight (12 hr), then transferred to a fresh LB liquid culture medium and further cultured at 30° C. for 12 hr.

The culture solution was diluted to a proper concentration and then spread on an LB plate. Forward primer C-P lyase_5UTR and reverse primer lyase_3DSR were used to screen clones without Gen gene.

The monoclones were selected to be sequenced. The strain were preserved and named as DH46ΔC-P lyase. DH46ΔC-P lyase is *E. coli* DH5 with C-P lyase genes being knocked out.

TABLE 3

Name of primers used in the present example and their nucleotide sequences

| Primer name | Nucleotide sequence (5'-3') | SEQ. ID. NO |
|---|---|---|
| C-P lyase_P15 | ccgaccagctacccaacacgctatc | 42 |
| C-P lyase_P13 | ggggatcctctagagtcgacgcagacgc cctgacggcgctgta | 43 |
| C-P lyase_P25 | gggtaccgagctcgaattctcagaattg ccttcgcggtgacggatgagg | 44 |
| C-P lyase_P23 | tcagcacacctccacatgagtggttc | 45 |
| C-P lyase_5UTR | tgctggatttcctctctcaacg | 46 |
| C-P lyase_Gen3 | atttaacataatatacattatgcgcacc | 47 |
| C-P lyase_3DSR | gctatcctcttcaaacttcgccagc | 48 |
| EcEPSPS_P35 | tccctgacgttacaacccatcgc | 49 |
| EcEPSPS_P33 | ggggatcctctagagtcgacgcactcca gggcaccttctgcgtg | 50 |
| EcEPSPS_P45 | ggtaccgagctcgaattctcagaattgc gaccatttgctgggcga | 51 |
| EcEPSPS_P43 | cggaggagtgatacgaatgtaatcg | 52 |
| EcES25 | gcgctgacagacttcatggttg | 53 |
| EcES23 | caacttacattgacaagcgacgc | 54 |

3. Knocking Out the EPSPS Gene of DH46ΔC-P Lyase (*E. coli* DH5α with C-P Lyase Genes being Knocked Out)

(1) Preparation of DH46ΔC-P Lyase Competent Cells

The preserved DH46ΔC-P lyase was subjected to streaking on an LB+Amp plate, and cultured at 30° C. overnight.

Positive monoclonal colonies were selected and inoculated in small amount of M9-sucrose liquid culture medium and cultured at shaking speed of 180 rpm and temperature of 30° C. overnight.

After culturing, they were inoculated in larger amount of M9 liquid culture medium (containing sucrose+100 μg/mL Amp+10 mM L-arabinose) at a ratio of 1:10, and cultured at 30° C. until OD600 of the culture reaches 0.7.

The above strain solution (containing DH46ΔC-P lyase) was cooled on ice for 20 min. The microbial cells were recovered by centrifuging at 4° C. and 4000 rpm, resuspended with 40 mL of pre-cooled 10% (v/v) glycerol, and repeatedly washed for 3 times. The supernatant was discarded. Then the residues were resuspended with 400 μL of pre-cooled 10% glycerol and divided and packed by 100 μL/tube.

(2) Amplification of Homologous PCR Fragment

Forward primer EcEPSPS_P35 and reverse primer EcEPSPS_P33 were used to conduct amplification with the genome DNA of the DH46ΔC-P lyase strain being used as a template. Product P3 fragment was obtained. See SEQ ID NO.8 for the nucleotide sequence of P3 fragment.

Forward primer EcEPSPS_P45 and reverse primer EcEPSPS_P43 were used to conduct amplification with the genome DNA of the DH46ΔC-P lyase being used as the template. Product P4 fragment was obtained. See SEQ ID NO.9 for the nucleotide sequence of P4 fragment.

P3 fragment and P4 fragment were purified through 1% agarose electrophoresis. Then they were added to plasmid containing Gen-resistant fragments in proportion to make a mixing pool which was used as a template for amplification using EcEPSPS_P35 and EcEPSPS_P43 as primers. Product PRE fragment with a length of 1607 bp was obtained. See SEQ ID NO.22 for its nucleotide sequence.

(3) Transformation by Heat Shock

50 μL of DH46ΔC-P lyase competent cells were gently mixed with 35 μL of purified PRE fragments. Then they were placed in a 0.1 cm pre-cooled electroporation cuvette and subjected to electric shock by Bio-Rad electroporator at 1.8 kV.

They were quickly added to 1 mL of M9-sucrose liquid culture medium containing 10 mM arabinose, cultured at 37° C. for 1 hr and then spread on LB solid culture medium so as to screen the recombinant strains which were at 30° C. cultured overnight. The next day, primers EcEPSPS_P35 and EcEPSPS_P43 were used to screen positive clones containing Gen gene to prove the presence of Gen gene.

The positive clones were inoculated in LB liquid culture medium and cultured at 37° C. overnight (12 hr), then transferred to fresh LB liquid culture medium and further cultured at 37° C. for 12 hr.

The culture solution was diluted to a proper concentration and then coated on a LB plate. Forward primer EcES25 and reverse primer EcES23 were used to screen clones without GM gene.

Monoclones were selected to be sequenced. The strain was preserved and named as DH5αΔPhnFGHΔEPSPS. DH5αΔPhnFGHΔEPSPS is a E. coli DH5α strain with C-P lyase genes and EPSPS gene being knocked out, i.e. EPSPS gene-and-C-P lyase genes-deleted strain.

It is to be noted that DH5αΔPhnFGHΔEPSPS is a knockout strain without antibiotic gene. Most of PhnF genes, all PhnG genes and part of PhnH genes and those genes which degrade phosphonates, typically glyphosate, in E. coli DH5α were knocked out. See SEQ ID NO.11 for the nucleic acid sequence fragments of the nucleic acid fragments of the upstream sequence connected to 5 terminal and the downstream sequence connected to 3 terminal of FRT DNA fragment. Located on site 1 to site 318 were 5 terminal of E. coli PhnF gene and its upstream sequence. The nucleotide sequence from site 319 to site 347 was FRT fragment. Located on site 348 to site 1021 were 3 terminal of E. coli PhnH gene and its downstream sequence. In addition, most of the EPSPS genes in DH5αΔPhnFGHΔEPSPS were replaced with FRT fragments, as shown in SEQ ID NO.12. Located on site 1 to site 357 was 5 terminal sequence of E. coli EPSPS gene. Located on site 358 to site 386 was FRT fragment. Located on site 387 to site 818 was terminal sequence of E. coli EPSPS gene 3.

Step 2, is to, using the EPSPS gene-and-C-P lyase genes-deleted strain obtained in step 1 of the present example as a host strain, introduce Glycine max EPSPS gene from Glycine max into the host strain, so as to obtain mutant strain, i.e. Glycine max EPSPS gene mutant library.

A conventional method was used to clone the Glycine max EPSPS gene to pADV5 vector which was then used to transform the host strain DH5αΔPhnFGHΔEPSPS.

The transformed DH5αΔPhnFGHΔEPSPS were inoculated to MA liquid culture medium (M9 basal culture medium+100 μg/mL Amp) and cultured at 37° C. and 300 r/min overnight.

The strain solution, which had become turbid, was subjected to radiation-induced mutagenesis, e.g. exposure to ultraviolet for 2-5 min, for the Glycine max EPSPS gene to mutate, so as to obtain corresponding Glycine max EPSPS mutant gene, and thus mutant strain is Glycine max EPSPS gene mutant library. Sure, this step may also be done by chemical mutagenesis, i.e. adding a chemical mutagen e.g. EMS or DES to a MA culture medium for the Glycine max EPSPS gene to mutate.

Step 3, is screening culture.

Five μL of the above strain solution containing mutant strain was added to screening culture medium and further cultured at 300 r/min and 37° C. overnight.

Step 4, is sequencing and verification.

Monoclonal resistant strains growing on the screening culture medium were screened and separated so as to check for glyphosate resistance, and they were sequenced and verified, giving glyphosate-resistant Glycine max EPSPS mutant gene sequences.

One of the Glycine max EPSPS mutant genes is taken as an example for explanation. As can be seen in SEQ ID NO.10, its nucleotide sequence consists of 1368 bases. This Glycine max EPSPS mutant gene (which is named as GmEM gene) is compared with wild type Glycine max EPSPS gene (which is named as GmE gene) in terms of their nucleotide sequences (as shown in SEQ ID NO.5) and the amino acid sequences they code. FIG. 4 shows the result. In this Glycine max EPSPS mutant gene, in a direction from 5' terminal to 3' terminal, a base "G" is inserted between site 6 and site 8, and a base "A" is deleted between site 45 and site 46, causing frameshift mutation on the bases from site 7 to site 44. Accordingly, mutation happens on bases from site 3 to site 15 (from amino acid terminal and carboxyl terminal) in the amino acid residue sequence coded by this fragment (as shown in FIG. 4). In addition, the base on site 629 mutates from "A" to "T", causing the amino acid residue on site 210 in the amino acid residue sequence to mutate from glutamic acid residue to valine residue. The base on site 1110 mutates from "A" to "G", while base on site 1125 mutates from "T" to "C", on both of which the mutation of the bases does not cause mutation of the corresponding amino acid residue they code.

For glyphosate resistance testing of *Glycine max* EPSPS mutant gene, *E. coli* (EPSPS gene-and-C-P lyase genes-deleted strain) respectively transformed with GmEM gene (experimental group) and GmE gene (control group) were inoculated to culture media containing 0 mM, 1 mM, 5 mM, 10 mM, 20 mM, 50 mM and 100 mM glyphosate to see the growth of *E. coli*. Table 4 shows the result.

TABLE 4

Growth saturation index of *E. coli* transformed with GmEM gene and GmE gene in culture media with different concentrations of glyphosate

| Gene | Growth saturation index | | | | | | |
|---|---|---|---|---|---|---|---|
| | 0 mM | 1 mM | 5 mM | 10 mM | 20 mM | 50 mM | 100 mM |
| GmE | 4 | 0 | 0 | 0 | 0 | 0 | 0 |
| GmEM | 4 | 4 | 4 | 4 | 4 | 3 | 0 |

As can be seen from Table 4, on the culture medium containing 0 mM glyphosate, both the experimental group (containing GmEM gene) and the control group (containing GmE gene) show normal growth (saturation index being 4); but on culture media containing 1 mM, 5 mM, 10 mM and 20 mM glyphosate, the strains in the control group cannot grow normally, whereas the experimental group shows normal growth (the saturation index being 4); on the culture medium containing 50 mM glyphosate, the strains in the control group cannot grow normally, whereas the experimental group shows vigorous growth (the saturation index being 3); on the culture medium containing 100 mM glyphosate, neither the experimental group nor the control group shows normal growth (the saturation indexes of both being 0). This indicates that the *Glycine max* EPSPS mutant gene (see SEQ ID NO.10 for its nucleotide sequence) obtained by screening in the present example can provide EPSPS gene-and-C-P lyase genes-deleted *E. coli* with glyphosate resistance so that the *E. coli* can grow on a culture medium containing up to 50 mM glyphosate.

The glyphosate-resistant *Glycine max* EPSPS mutant gene obtained by screening with the method for screening glyphosate-resistant mutant genes provided by the present example of the present disclosure is resistant to 50 mM glyphosate. See SEQ ID NO.10 for its nucleotide sequence.

Directly using the glyphosate-resistant *Glycine max* EPSPS mutant gene (see SEQ ID NO.10 for its nucleotide sequence) obtained by screening with the method for screening glyphosate-resistant mutant genes provided by the present example of the present disclosure to transform soybean or rice or other plants provides the transformed plants with glyphosate resistance.

Example 3

The present example provides a knock-out strain. Specifically, the knock-out strain is an EPSPS gene-and-C-P lyase genes-deleted strain. The EPSPS gene-and-C-P lyase genes-deleted strain is obtained by knocking out the EPSPS gene and C-P lyase genes in any one of *E. coli* DH5α, TOP10 and BL21 by a gene knock-out technology. Specifically, the gene knock-out method used in the present example is same as that used in Example 1 or Example 2.

The EPSPS gene-and-C-P lyase genes-deleted strain provided by the present example may be applied in testing the functions of EPSPS gene from a target plant. Specifically, the EPSPS gene-and-C-P lyase genes-deleted strain of the present example is used as a host strain. The EPSPS gene from the target plant is introduced into the host strain which are then placed on basal culture media being free of amino acid or protein i.e. limiting culture media for culture. It is demonstrated that the EPSPS gene from the target plant is capable of expressing EPSPS (5-enolpyruvylshikimate-3-phosphate synthase) and the EPSPS has normal biological activity, If normal growth of colonies are observed on the limiting culture media.

The EPSPS gene-and-C-P lyase genes-deleted strain provided by the present example may also be applied in testing the glyphosate resistance of the EPSPS gene from a target plant. Specifically, the EPSPS gene-and-C-P lyase genes-deleted strain of the present example is used as a host strain. The EPSPS gene of the target plant is introduced to the host strain which is then placed on M9 culture media containing different concentrations of glyphosate for culture, e.g. on M9 culture media containing 10 mM, 20 mM and 50 mM glyphosate, so as to test the glyphosate resistance of the EPSPS gene from the target plant.

The EPSPS gene-and-C-P lyase genes-deleted strain provided by the present example may be applied in screening glyphosate-resistant EPSPS mutant gene from a target plant. See the method for screening glyphosate-resistant EPSPS mutant genes provided in Example 1 or Example 2.

To sum up, by the screening method provided by the examples of the present disclosure, an EPSPS gene-and-C-P lyase genes-deleted strain is constructed, an exogenous EPSPS gene from a target plant is introduced into the EPSPS gene-and-C-P lyase genes-deleted strain which is used as a host strain, so as to obtain mutant strain containing an exogenous EPSPS mutant gene, i.e. an exogenous EPSPS gene mutant library, and then glyphosate-resistant EPSPS mutant genes are screened from the exogenous EPSPS gene mutant library. Due to fast reproduction speed and small size of *E. coli*, the screening method of the present disclosure overcomes the problems of long period and large acreage needed in the current field screening methods. Therefore, the screening method of the present disclosure is characterized by short period, very small space, simple operation, in term of operation of directed screening of glyphosate-resistant EPSPS mutant gene. Furthermore, using EPSPS gene-and-C-P lyase genes-deleted *E. coli* as a host strain, the screening method provided of the present disclosure effectively avoids the situation where resistance to glyphosate is developed as a result of mutation of the EPSPS genes and C-P lyase genes of the host strain themselves. Therefore, the screening results are more scientific and reliable. The screened gene mutant of EPSPS gene from plants can substantially improve the screening speed and shorten the time. Normally, it takes only 1-2 weeks to finish the screening and obtain mutant genes resistant to glyphosate, reducing the cost of screening. In addition, the glyphosate-resistant mutant gene obtained by the screening method provided by the present disclosure can be also used to transform corresponding plant species. The present method breaks through the bottleneck of most existing methods, only resistant genes from microorganism can be transformed to crops, helping elimination of the bias that the public have against transgenic plants, and thus facilitating the development and promotion of transgenic technology. Furthermore, the EPSPS gene-and-C-P lyase genes-deleted strain provided by the present disclosure can be applied in testing the functions of an EPSPS gene from a plant—and also in testing the glyphosate resistance of an EPSPS gene from a plant. The application is convenient and the result is more scientific and reliable.

The above description only shows the preferable embodiments of the present disclosure and is not intended to limit the present disclosure. Various modifications and variations of the present disclosure will occur to those skilled in the art. Any modifications, equivalent replacements and improvements made within the spirit and principle of the present disclosure shall be encompassed by the scope of protection of the present disclosure.

The invention claimed is:

1. A method for screening glyphosate-resistant genes, comprising:
   knocking out interference genes of a source strain by a gene knockout technology to obtain a knock-out strain, wherein the source strain is one of *E. coli* DH5a, *E. coli* TOP10 and *E. coli* BL21, the interference genes comprise EPSPS gene and C-P lyase genes, and the knock-out strain is an EPSPS gene-and-C-P lyase genes-deleted strain;
   cloning an exogenous EPSPS gene into the knock-out strain for screening of glyphosate resistance, wherein the exogenous EPSPS gene is a wild-type or mutated EPSPS gene coming from a target plant;
   culturing the knock-out strain with cloned exogenous EPSPS on at least one screening culture medium containing glyphosate, to identify resistant strains having resistance to glyphosate; and
   isolating individual colonies of the resistant strains having resistance to glyphosate and sequencing the cloned EPSPS genes from the resistant strains, so as to obtain one or more glyphosate-resistant EPSPS mutant genes, wherein a method for knocking out the C-P lyase genes in *E. coli* comprises the step of transferring the nucleotide fragment as shown in SEQ ID NO.16 into *E. coli* to obtain an *E. coli* with the C-P lyase genes being knocked out.

2. The method for screening glyphosate-resistant gene according to claim 1, wherein the mutated EPSPS gene is obtained by chemical mutagenesis treatment or radiation-induced mutagenesis treatment.

3. The method for screening glyphosate-resistant gene according to claim 1, wherein the mutated EPSPS gene is obtained by conducting a PCR by mismatch PCR method or DNA Shuffling method using the exogenous EPSPS gene as a template, so as to obtain the mutated EPSPS gene.

4. The method for screening glyphosate-resistant gene according to claim 1, wherein the target plant is rice, soybean, wheat, corn, barley, sorghum, tobacco, cotton, sweet potato, poplar, potato, Chinese cabbage, cabbage or green pepper.

5. A glyphosate-resistant EPSPS mutant gene obtained by the method according to claim 1, wherein the EPSPS mutant gene encodes a glyphosate-resistant EPSPS having the amino acid sequence as encoded by the nucleotide sequence as shown in SEQ ID NO.4 or SEQ ID NO.10.

6. The glyphosate-resistant EPSPS mutant gene according to claim 5, wherein the glyphosate-resistant EPSPS mutant gene enables a plant to becomes resistant to glyphosate by transforming the plant.

7. The glyphosate-resistant EPSPS mutant gene according to claim 5, wherein the mutated EPSPS gene is obtained by chemical mutagenesis treatment or radiation-induced mutagenesis treatment.

8. The glyphosate-resistant EPSPS mutant gene according to claim 5, wherein the mutated EPSPS gene is obtained by conducting a PCR by mismatch PCR method or DNA Shuffling method using the exogenous EPSPS gene as a template, so as to obtain the mutated EPSPS gene.

9. The glyphosate-resistant EPSPS mutant gene according to claim 5, wherein the target plant is rice[, soybean, wheat, corn, barley, sorghum, tobacco, cotton, sweet potato, poplar, potato, Chinese cabbage, cabbage or green pepper].

10. The glyphosate-resistant EPSPS mutant gene according to claim 7, wherein the glyphosate-resistant EPSPS mutant gene enables a plant to becomes resistant to glyphosate by transforming the plant.

11. The glyphosate-resistant EPSPS mutant gene according to claim 8, wherein the glyphosate-resistant EPSPS mutant gene enables a plant to becomes resistant to glyphosate by transforming the plant.

12. The glyphosate-resistant EPSPS mutant gene according to claim 9, wherein the glyphosate-resistant EPSPS mutant gene enables a plant to becomes resistant to glyphosate by transforming the plant.

\* \* \* \* \*

SEQUENCE LISTING

<160> NUMBER OF SEQ ID NOS: 54

<210> SEQ ID NO 1
<211> LENGTH: 1365
<212> TYPE: DNA
<213> ORGANISM: Oryza sativa

<400> SEQUENCE: 1

| | | | | | | |
|---|---|---|---|---|---|---|
| atggcgtcca | acgccgcggc | tgcggcggcg | aaggcggagg | agatcgtgct | ccagcccatc | 60 |
| agggagatct | ccggggcggt | tcagctgcca | gggtccaagt | cgctctccaa | caggatcctc | 120 |
| ctcctctccg | ccctctccga | gggcacaaca | gtggtggaca | acttgctgaa | cagtgaggat | 180 |
| gttcactaca | tgcttgaggc | cctgaaagcc | ctcgggctct | ctgtggaagc | agataaagtt | 240 |
| gcaaaaagag | ctgtagtcgt | tggctgtggt | ggcaagtttc | ctgttgagaa | ggatgcgaaa | 300 |
| gaggaagtgc | aactcttctt | ggggaacgct | gcgactgcaa | tgcgactctt | gacagcagcc | 360 |
| gtgactgctg | ctggtggaaa | tgcaacttat | gtgcttgatg | gagtgccacg | aatgagggag | 420 |
| agaccgattg | gtgacttggt | tgtcgggttg | aaacaacttg | gtgcggatgt | cgactgtttc | 480 |
| cttggcactg | aatgcccacc | tgttcgtgtc | aagggaattg | gaggacttcc | tggtggcaag | 540 |
| gttaagctct | ctggttccat | cagcagtcag | tacttgagtg | ccttgctgat | ggctgctcct | 600 |
| ttggcccttg | gggatgtgga | gatcgaaatc | attgacaaac | taatctccat | tccttacgtt | 660 |
| gaaatgacat | tgagattgat | ggagcgtttt | ggtgtgaagg | cagagcattc | tgatagttgg | 720 |
| gacagattct | atattaaggg | agggcagaag | tacaaatctc | ctggaaatgc | ctatgttgaa | 780 |
| ggtgatgcct | caagcgcgag | ctatttcttg | gctggtgctg | caatcactgg | aggcactgtg | 840 |
| acagttcaag | gttgtggtac | gaccagtttg | cagggtgatg | tcaaatttgc | tgaggtactt | 900 |
| gagatgatgg | gagcaaaggt | tacatggact | gacaccagtg | taaccgtaac | tggtccacca | 960 |
| cgtgagcctt | atgggaagaa | acacctgaaa | gctgttgatg | tcaacatgaa | caaaatgcct | 1020 |
| gatgttgcca | tgacccttgc | cgttgttgca | ctcttcgctg | atggtccaac | tgctatcaga | 1080 |
| gatgtggctt | cctggagagt | aaaggaaacc | gaaaggatgg | ttgcaattcg | gaccgagcta | 1140 |
| acaaagctgg | gagcatcggt | tgaagaaggt | cctgactact | gcatcatcac | cccaccggag | 1200 |
| aagctgaaca | tcacggcaat | cgacacctac | gatgatcaca | ggatggccat | ggccttctcc | 1260 |
| ctcgctgcct | gcgccgacgt | gcccgtgacg | atcagggacc | ctggttgcac | ccgcaagacc | 1320 |
| ttccccaact | acttcgacgt | tctaagcact | ttcgtcagga | actga | | 1365 |

<210> SEQ ID NO 2
<211> LENGTH: 1368
<212> TYPE: DNA
<213> ORGANISM: Artificial Sequence
<220> FEATURE:
<223> OTHER INFORMATION: Spectinomycin-streptomycin adenyltransferase

<400> SEQUENCE: 2

| | | | | | | |
|---|---|---|---|---|---|---|
| ttgacagcta | gctcagtcct | aggtataata | ctagttaacg | gcatgtacat | ctgccgtttt | 60 |
| agagctagaa | atagcaagtt | aaaataaggc | tagtccgtta | tcaacttgaa | aaagtggcac | 120 |
| cgagtcggtg | cttttttga | attctctaga | gtcgacctgc | agaagcttag | atccttgaca | 180 |
| gctagctcag | tcctaggtat | aatactagtc | aggtcgccag | cctgagcggg | ttttagagct | 240 |

```
agaaatagca agttaaaata aggctagtcc gttatcaact tgaaaaagtg gcaccgagtc    300 ggtgctttt  ttgaattctc tagagtcgac ctgcagaagc ttagatcttt tgccctgctg    360
acttttgagg aaatccacat gtcattacca cactgcccaa aatgcaactc cgaatacact    420
tacgaagata acggcatgta catctgctaa tacgactcac tatagggaga atgagggaag    480
cggtgatcgc cgaagtatcg actcaactat cagaggtagt tggcgtcatc gagcgccatc    540
tcgaaccgac gttgctggcc gtacatttgt acggctccgc agtggatggc ggcctgaagc    600
cacacagtga tattgatttg ctggttacgg ttacggtgac cgtaaggctt gatgaaacaa    660
cgcggcgagc tttgatcaac gacctttggg aaacttcggc ttcccctgga gagagcgaga    720
ttctccgcgc tgtagaagtc accattgttg tgcacgacga catcattccg tggcgttatc    780
cagctaagcg cgaactgcaa tttggagaat ggcagcgcaa tgacattctt gcaggtatct    840
tcgagccagc cacgatcgac attgatctgg ctatcttgct gacaaaagca agagaacata    900
gcgttgcctt ggtaggtcca gcggcggagg aactctttga tccggttcct gaacaggatc    960
tatttgaggc gctaaatgaa accttaacgc tatggaactc gccgcccgac tgggctggcg    1020
atgagcgaaa tgtagtgctt acgttgtccc gcatttggta cagcgcagta accggcaaaa    1080
tcgcgccgaa ggatgtcgct gccgactggg caatggagcg cctgccggcc cagtatcagc    1140
ccgtcatact tgaagctaga caggcttatc ttggacaaga agaagatcgc ttggcctcgc    1200
gcgcagatca gttggaagaa tttgtccact acgtgaaagg cgagatcacc aaggtagtcg    1260
gcaaataagg acgcatgtta cgtctcaccg gcgcgggcat tgccgaagaa cgaatgatcg    1320
ccccgcagct gccggagtgc attctgtacg aactcaccga gcgcccgc                 1368

<210> SEQ ID NO 3
<211> LENGTH: 1509
<212> TYPE: DNA
<213> ORGANISM: Artificial Sequence
<220> FEATURE:
<223> OTHER INFORMATION: Gentamicin 3'-acetyltransferase

<400> SEQUENCE: 3
ttgacagcta gctcagtcct aggtataata ctagtgatgg cactattaat ctgccgtttt     60
agagctagaa atagcaagtt aaaataaggc tagtccgtta tcaacttgaa aaagtgacac    120
cgagtcggtg cttttttga   attctctaga gtcgacctgc agaagcttag atccttgaca    180
gctagctcag tcctaggtat aatactagta ttatttcgag cagctggcgg ttttagagct    240
agaaatagca agttaaaata aggctagtcc gttatcaact tgaaaaagtg gcaccgagtc    300 ggtgctttt  ttgaattctc tagagtcgac ctgcagaagc ttagatctag ccagcctgtg    360 gggttttat  ttctgttgta gagagttgag ttcatggaat ccctgacgtt acaacccatc    420
gctcgtgtcg atggcactat taatctgcag aggcggtttg cgtattgggc gcatgcataa    480
aaactgttgt aattcattaa gcattctgcc gacatggaag ccatcacaaa cggcatgatg    540
aacctgaatc gccagcggca tcagcacctt gtcgccttgc gtataatatt tgcccatgga    600
cgcacaccgt ggaaacggat gaaggcacga acccagttga cataagcctg ttcggttcgt    660
aaactgtaat gcaagtagcg tatgcgctca cgcaactggt ccagaacctt gaccgaacgc    720
agcggtggta acggcgcagt ggcggttttc atggcttgtt atgactgttt ttttgtacag    780
tctatgcctc gggcatccaa gcagcaagcg cgttacgccg tgggtcgatg tttgatgtta    840
tggagcagca acgatgttac gcagcagcaa cgatgttacg cagcagggca gtcgccctaa    900
```

```
aacaaagtta ggtggctcaa gtatgggcat cattcgcaca tgtaggctcg gccctgacca    960
agtcaaatcc atgcgggctg ctcttgatct tttcggtcgt gagttcggag acgtagccac   1020
ctactcccaa catcagccgg actccgatta cctcgggaac ttgctccgta gtaagacatt   1080
catcgcgctt gctgccttcg accaagaagc ggttgttggc gctctcgcgg cttacgttct   1140
gcccaagttt gagcagccgc gtagtgagat ctatatctat gatctcgcag tctccggaga   1200
gcaccggagg cagggcattg ccaccgcgct catcaatctc ctcaagcatg aggccaacgc   1260
gcttggtgct tatgtgatct acgtgcaagc agattacggt gacgatcccg cagtggctct   1320
ctatacaaag ttgggcatac gggaagaagt gatgcacttt gatatcgacc caagtaccgc   1380
cacctaacaa ttcgttcaag ccgagatcac ggattagcca ggcagcctga atgaacaacg   1440
ggcaataaat agccaaatct ttctttatca aaacgtcggc acattgtcgg cgttttttt   1500 cggaccttg                                                          1509
```

<210> SEQ ID NO 4
<211> LENGTH: 1365
<212> TYPE: DNA
<213> ORGANISM: Artificial Sequence
<220> FEATURE:
<223> OTHER INFORMATION: Oryza sativa EPSPS mutant

<400> SEQUENCE: 4

```
atggcgtcca acgccgcggc tgcggcggcg aaggcggagg agatcgtgct ccagcccatc     60
agggagatct ccggggcggt tcagctgcca gggtccaagt cgctctccaa caggatcctc    120
ctcctctccg ccctctccga gggcacaaca gtggtggaca acttgctgaa cagtgaggat    180
gttcactaca tgcttgaggc cctgaaaggc ctcgggctct ctgtggaagc agataaagtc    240
gcaaaaagag ctgtagtcgt tggctgtggt ggcaagtttc ctgttgagaa ggatgcgaaa    300
gaggaagtgc aactcttctt ggggaacgct gcgactgcaa tgcgatcctt gacagcagcc    360
gtgactgctg ctggtggaaa tgcaacttat gtgctcgatg gagtgccacg aatgagggag    420
agaccgattg gtgacttggt tgtcgggttg aagcaacttg gtgcggatgt cgactgtttc    480
cttggcactg aatgcccacc tgttcgtgtc aaggaattga gggacttcc tggtggcaag    540 gttaagctct ctggttccat cagcagtcag tacttgagtg ccttgctgat ggctgctcct    600
ttggctcttg gggatgtgga gatcgaaatc attgacaaac taatctccat tccttacgtt    660
gaaatgacat tgagattgat ggagcgtttt ggtgtgaagg cagagcattc tgatagttgg    720
gacagattct atattaaggg agggcagaag tacaaatctc ctggaaatgc ctatgttgaa    780
ggtgatgcct caagcgcgag ctatttcttg gctggtgctg caatcactgg gggcactgtg    840
acagttcaag ttgtggtac gaccagtttg caggtgatg tcaaatttgc tgaggtactt    900
gagatgatgg agcaaaggt tacatggact gacaccagtg taaccgtaac tggtccacca    960
cgtgagcctt atgggaagaa acacctgaaa gctgttgatg tcaacatgaa caaaatgcct   1020
gatgttgcca tgaccttgc cgttgttgca ctcttcgctg atggtccaac tgctatcaga   1080
gatgtggctt cctggagagt aaaggaaacc gaaaggatgg ttgcaattcg gaccgagcta   1140
acaaagctgg gagcatcgt tgaagaaggt cctgactact gcatcatcac cccaccggag   1200
aagctgaaca tcacggcaat cgacacctac gatgatcaca ggatggccat ggccttctcc   1260
ctcgctgcct cgccgacgt gcccgtgacg atcagggacc tggttgcac ccgcaagacc   1320 ttccccaact acttcgacgt tctaagcact ttcgtcagga actga                  1365
```

<210> SEQ ID NO 5
<211> LENGTH: 1368
<212> TYPE: DNA
<213> ORGANISM: Glycine max

<400> SEQUENCE: 5

```
atggatagcg tggcggcggc ggaaaaaccg agcaccagcc cggaaattgt gctggaaccg      60
attaaagatt ttagcggcac cattaccctg ccgggcagca aaagcctgag caaccgcatt     120
ctgctgctgg cggcgctgag cgaaggcacc accgtggtgg ataacctgct gtatagcgaa     180
gatattcatt atatgctggg cgcgctgcgc accctgggcc tgcgcgtgga agatgataaa     240
accaccaaac aggcgattgt ggaaggctgc ggcggcctgt ttccgaccag caagaaagc      300
aaagatgaaa ttaacctgtt tctgggcaac gcggcgaccg cgatgcgcag cctgaccgcg     360
gcggtggtgg cggcgggcgg caacgcgagc tatgtgctgg atggcgtgcc gcgcatgcgc     420
gaacgcccga ttggcgatct ggtggcgggc ctgaaacagc tgggcgcgga tgtggattgc     480
tttctgggca ccaactgccc gccggtgcgc gtgaacggca aaggcggcct gccgggcggc     540
aaagtgaaac tgagcggcag cgtgagcagc cagtatctga ccgcgctgct gatggcggcg     600
ccgctgcgc tggcgatgt ggaaattgaa attgtggata aactgattag cgtgccgtat       660
gtggaaatga ccctgaaact gatggaacgc tttggcgtga gcgtggaaca tagcggcaac     720
tgggatcgct ttctggtgca tggcggccag aaatataaaa gcccgggcaa cgcgtttgtg     780
gaaggcgatg cgagcagcgc gagctatctg ctggcgggcg cggcgattac cggcggcacc     840
attaccgtga acggctgcgg caccagcagc ctgcagggcg atgtgaaatt tgcggaagtg     900
ctggaaaaaa tgggcgcgaa agtgacctgg agcgaaaaca gcgtgaccgt gagcggcccg     960
ccgcgcgatt ttagcggccg caaagtgctg cgcggcattg atgtgaacat gaacaaaatg    1020
ccggatgtgg cgatgaccct ggcggtggtg gcgctgtttg cgaacggccc gaccgcgatt    1080
cgcgatgtgg cgagctggcg cgtgaaagaa accgaacgca tgattgcgat ttgcaccgaa    1140
ctgcgcaaac tgggcgcgac cgtggaagaa ggcccggatt attgcgtgat taccccgccg    1200
gaaaaactga cgtgaccgc gattgatacc tatgatgatc atcgcatggc gatggcgttt    1260
agcctggcgg cgtgcggcga tgtgccggtg accattaaag atccgggctg cacccgcaaa    1320
acctttccgg attattttga agtgctggaa cgcctgacca aacattaa                 1368
```

<210> SEQ ID NO 6
<211> LENGTH: 218
<212> TYPE: DNA
<213> ORGANISM: Artificial Sequence
<220> FEATURE:
<223> OTHER INFORMATION: Escherichia coli gemonic fragment 1

<400> SEQUENCE: 6

```
ccgaccagct acccaacacg ctatcaagag atagccgcaa aacttgagca ggagcttcgt      60
caacactacc gctgcggcga ctatcttccc gccgagcagc aactggcagc cgctttgag     120
gtgaatcgcc acaccctgcg ccgcgccatc gaccaactgg tggaaaaagg ctgggtacag    180
cgccgtcagg gcgtctgcgt cgactctaga ggatcccc                            218
```

<210> SEQ ID NO 7
<211> LENGTH: 336
<212> TYPE: DNA
<213> ORGANISM: Artificial Sequence
<220> FEATURE:
<223> OTHER INFORMATION: Escherichia coli gemonic fragment 2

<400> SEQUENCE: 7

```
gggtaccgag ctcgaattct cagaattgcc ttcgcggtga cggatgaggc gatttccagc    60
gaacagctca acgccctttc caccggcacc gccgttgcgc cggaagcggg tgcgacgctg   120
attttacagg tcgccagcct gagcggcgga cgcatgttgc gccttactgg tgcgggtatt   180
gccgaagaac gaatgatcgc tccgcagctg ccggagtgca ttctgcacga actcaccgag   240
cgcccgcatc cgttcccgct cggcatcgac ctgatcctga cctgtggcga gcgcctgctg   300
gctattccgc gaaccactca tgtggaggtg tgctga                             336
```

<210> SEQ ID NO 8
<211> LENGTH: 284
<212> TYPE: DNA
<213> ORGANISM: Artificial Sequence
<220> FEATURE:
<223> OTHER INFORMATION: Escherichia coli gemonic fragment 3

<400> SEQUENCE: 8

```
tccctgacgt tacaacccat cgctcgtgtc gatggcacta ttaatctgcc cggttccaag    60
agcgtttcta accgcgcttt attgctggcg gcattagcac acggcaaaac agtattaacc   120
aatctgctgg atagcgatga cgtgcgccat atgctgaatg cattaacagc gttagggtga   180
agctatacgc tttcagccga tcgtacgcgt tgcgaaatta tcggtaacgg cggtccatta   240
ctccagggca ccttctgcgt gggggatcct ctagagtcga cgca                    284
```

<210> SEQ ID NO 9
<211> LENGTH: 289
<212> TYPE: DNA
<213> ORGANISM: Artificial Sequence
<220> FEATURE:
<223> OTHER INFORMATION: Escherichia coli gemonic fragment 4

<400> SEQUENCE: 9

```
gggtaccgag ctcgaattct cagaattgcg accatttgct ggggcgatga ttatatttcc    60
tgcacgcgtg gtgaactgaa cgctattgat atggatatga accatattcc tgatgcggcg   120
atgaccattg ccacggcggc gttatttgca aaaggcacca ccacgctgcg caatatctat   180
aactggcgtg ttaaagagac cgatcgcctg tttgcgatgg caacagaact gcgtaaagtc   240
ggcgcggaag tggaagaggg gcaccggagg agtgatacga atgtaatcg              289
```

<210> SEQ ID NO 10
<211> LENGTH: 1368
<212> TYPE: DNA
<213> ORGANISM: Artificial Sequence
<220> FEATURE:
<223> OTHER INFORMATION: Glycine max EPSPS mutant

<400> SEQUENCE: 10

```
atggatgagc gtggcggcgg cggaaaaacc gagcaccagc ccggaattgt gctggaaccg    60
attaaagatt ttagcggcac cattaccctg ccgggcagca aaagcctgag caaccgcatt   120
ctgctgctgg cggcgctgag cgaaggcacc accgtggtgg ataacctgct gtatagcgaa   180
gatattcatt atatgctggg cgcgctgcgc accctgggcc tgcgcgtgga agatgataaa   240
accaccaaac aggcgattgt ggaaggctgc ggcggcctgt tccgaccagc aaagaaagc   300 aaagatgaaa ttaacctgtt tctgggcaac gcggcgaccg cgatgcgcag cctgaccgcg   360
gcggtggtgg cggcgggcgg caacgcgagc tatgtgctgg atggcgtgcc gcgcatgcgc   420
gaacgcccga ttggcgatct ggtggcgggc ctgaaacagc tgggcgcgga tgtggattgc   480
```

```
tttctgggca ccaactgccc gccggtgcgc gtgaacggca aaggcggcct gccgggcggc    540
aaagtgaaac tgagcggcag cgtgagcagc cagtatctga ccgcgctgct gatggcggcg    600
ccgctggcgc tgggcgatgt ggaaattgta attgtggata aactgattag cgtgccgtat    660
gtggaaatga ccctgaaact gatggaacgc tttggcgtga gcgtggaaca tagcggcaac    720
tgggatcgct ttctggtgca tggcggccag aaatataaaa gcccgggcaa cgcgtttgtg    780
gaaggcgatg cgagcagcgc gagctatctg ctggcgggcg cggcgattac cggcggcacc    840
attaccgtga acggctgcgg caccagcagc ctgcagggcg atgtgaaatt tgcggaagtg    900
ctggaaaaaa tgggcgcgaa agtgacctgg agcgaaaaca gcgtgaccgt gagcggcccg    960
ccgcgcgatt ttagcggccg caaagtgctg cgcggcattg atgtgaacat gaacaaaatg   1020
ccggatgtgg cgatgaccct ggcggtggtg gcgctgtttg cgaacggccc gaccgcgatt   1080
cgcgatgtgg cgagctggcg cgtgaaagag accgaacgca tgatcgcgat ttgcaccgaa   1140
ctgcgcaaac tgggcgcgac cgtggaagaa ggcccggatt attgcgtgat taccccgccg   1200
gaaaaactga acgtgaccgc gattgatacc tatgatgatc atcgcatggc gatggcgttt   1260
agcctggcgg cgtgcggcga tgtgccggtg accattaaag atcccgggctg cacccgcaaa   1320 accttttccgg attattttga agtgctggaa cgcctgacca aacattaa                1368
```

<210> SEQ ID NO 11
<211> LENGTH: 1021
<212> TYPE: DNA
<213> ORGANISM: Artificial Sequence
<220> FEATURE:
<223> OTHER INFORMATION: C-P lyase knock-out fragment

<400> SEQUENCE: 11

```
aacctgcgcc ctgatggtgc ttatcatcgt cacggtcagc ctgctggatt tcctctctca     60
acggttgcgt aagcacttta tctgataagc gaggcattga tatctatgca cttgtctaca    120
catccgacca gctacccaac acgctatcaa gagatagccg caaaacttga gcaggagctt    180
cgtcaacact accgctgcgg cgactatctt cccgccgagc agcaactggc agcgcgcttt    240
gaggtgaatc gccacaccct gccgcgcgcc atcgaccaac tggtggaaaa aggctgggta    300
cagcgccgtc agggcgtctg gtgcgcataa tgtatattat gttaaatcct tcgcggtgac    360
ggatgaggcg atttccagcg aacagctcaa cgcccttttcc accggcaccg ccgttgcgcc    420
ggaagcgggt gcgacgctga ttttacaggt cgccagcctg agcggcggac gcatgttgcg    480
ccttactggt gcgggtattg ccgaagaacg aatgatcgct ccgcagctgc cggagtgcat    540
tctgcacgaa ctcaccgagc gcccgcatcc gttcccgctc ggcatcgacc tgatcctgac    600
ctgtggcgag cgcctgctgg ctattccgcg aaccactcat gtggaggtgt gctgatgtac    660
gttgccgtga agggggcga gaaggcgatc gacgccgccc acgccctgca agagagccga    720
cgccgaggcg ataccgattt gcccgaactg agcgtcgccc agattgaaca gcagcttaac    780
ctcgcggtag atcgcgtgat gaccgaaggc ggcattgccg accgcgaact ggcggcgctg    840 gcgctgaaaac aggccagcgg cgataacgtt gaagcgattt tcctgctgcg cgcctaccgc    900
accacgttgg cgaagctggc ggtaagcgag ccgctcgaca ccaccgggat gcgtctcgaa    960
cgccgtatct ccgccgttta taaagacatt cccggcggcc agctgcttgg cccaacctac   1020
g                                                                   1021
```

<210> SEQ ID NO 12

```
<211> LENGTH: 818
<212> TYPE: DNA
<213> ORGANISM: Artificial Sequence
<220> FEATURE:
<223> OTHER INFORMATION: EPSPS knock-out fragment

<400> SEQUENCE: 12
atggaatccc tgacgttaca accgaaattt tgcttaatcc ccacagccag cctgtggggt      60
ttttatttct gttgtagaga gttgagttca tggaatccct gacgttacaa cccatcgctc     120
gtgtcgatgg cactattaat ctgcccggtt ccaagagcgt ttctaaccgc gctttattgc     180
tggcggcatt agcacacggc aaaacagtat taaccaatct gctggatagc gatgacgtgc     240
gccatatgct gaatgcatta acagggttag gggtaagcta tacgctttca gccgatcgta     300
cgcgttgcga aattatcggt aacggcggtc cattacacgc agaaggtgcc ctggagttgg     360
tgcgcataat gtatattatg ttaaatgcga ccatttgctg gggcgatgat tatatttcct     420
gcacgcgtgg tgaactgaac gctattgata tggatatgaa ccatattccc gatgcggcga     480
tgaacattgc cacggcggcg ttatttgcaa aaggcaccac cacgctgcgc aatatctata     540
actggcgtgt taaagaaacc gatcgcctgt tgcgatggc aacagaactg cgtaaagtcg      600
gtgcggaagt agaagagggg cacgattaca ttcgtatcac tccaccggaa aaactgaact     660 tgccgagat cgcgacatac aatgatcacc ggatggcgat gtgtttctcg ctggtggcgt      720
tgtcagatac accagtgacg attcttgatc ccaaatgcac ggccaaaaca tttccggatt     780
atttcgagca gctggcgcgg attagccagg cagcctga                             818

<210> SEQ ID NO 13
<211> LENGTH: 525
<212> TYPE: DNA
<213> ORGANISM: Artificial Sequence
<220> FEATURE:
<223> OTHER INFORMATION: Escherichia coli gemonic fragment 5

<400> SEQUENCE: 13
agctgtaaca ggcgttcagc ctcctgactt aactcataca gggtctgtgt gtacatagaa      60
aattcttcct taaagcaaat tttgttattt tatttagcca gattgttttt gagttctgtt     120
ttcggctttt ataattactg caagaaataa ttttatattt agtgtgttgt tttttatcag     180
aataaataac gtcttctgat acgtttaaaa cgtcagaaag ataaaaatat catgtgaatt     240 aaaaaagaa caagtagagc attaacatta tcttaaataa taaatagagg caaaagatt      300 attttctttt tgcgtttcct ttcaaatgaa aacgatcgtc gtctaaaatc agcagtaccc     360
ccgacaaact cagggatttt gtgtataatt gcggcctttt tcggcaatct gccgtttttt     420
ggcgcttttg ccctgctgac ttttgaggaa atccacatgt cattaccaca ctgcccaaaa     480
tgcaactccg aatacaccta cgaagataac ggcatgtaca tctgc                     525

<210> SEQ ID NO 14
<211> LENGTH: 503
<212> TYPE: DNA
<213> ORGANISM: Artificial Sequence
<220> FEATURE:
<223> OTHER INFORMATION: Escherichia coli gemonic fragment 6

<400> SEQUENCE: 14
ggacgcatgt tacgtctcac cggcgcgggc attgccgaag aacgaatgat cgccccgcag      60
ctgccggagt gcattctgta cgaactcacc gagcgcccgc acccgttccc gctcggcatc     120
gacctgatcc tgacctgcgg cgagcgcctg ctggctattc cgcgaaccac gcatgtggag     180
```

```
gtgtgctgat gtacgttgcc gtgaaagggg gcgaaaaggc gatcgatgcc gcccacgccc      240
tgcaagagag ccgacgccgg ggcgataccg atttgcctga actgagcgtc gcccagattg      300
aacagcagct taacctcgca gtagatcgcg tgatgaccga aggcggcatt gccgaccgcg      360
aactggcggc gctggcgctg aaacaggcca gcggcgataa cgtcgaagca attttcctgc      420
tgcgcgccta ccgcaccacg ctggcgaagc tcgcggtaag cgagccgctc gacaccacgg      480
agatgcgtct cgaacggcgt att                                              503

<210> SEQ ID NO 15
<211> LENGTH: 900
<212> TYPE: DNA
<213> ORGANISM: Artificial Sequence
<220> FEATURE:
<223> OTHER INFORMATION: Gentamicin 3'-acetyltransferase

<400> SEQUENCE: 15
ctccgaatac acttacgaag ataacggcat gtacatctgc taatacgact cactataggg       60
agaatgaggg aagcggtgat cgccgaagta tcgactcaac tatcagaggt agttggcgtc      120
atcgagcgcc atctcgaacc gacgttgctg gccgtacatt tgtacggctc cgcagtggat      180
ggcggcctga agccacacag tgatattgat ttgctggtta cggttacggt gaccgtaagg      240
cttgatgaaa caacgcggcg agctttgatc aacgaccttt tggaaacttc ggcttcccct      300
ggagagagcg agattctccg cgctgtagaa gtcaccattg ttgtgcacga cgacatcatt      360
ccgtggcgtt atccagctaa gcgcgaactg caatttggag aatggcagcg caatgacatt      420
cttgcaggta tcttcgagcc agccacgatc gacattgatc tggctatctt gctgacaaaa      480
gcaagagaac atagcgttgc cttggtaggt ccagcggcgg aggaactctt tgatccggtt      540
cctgaacagg atctatttga ggcgctaaat gaaaccttaa cgctatggaa ctcgccgccc      600
gactgggctg gcgatgagcg aaatgtagtg cttacgttgt cccgcatttg gtacagcgca      660
gtaaccggca aaatcgcgcc gaaggatgtc gctgccgact gggcaatgga gcgcctgccg      720
gcccagtatc agcccgtcat acttgaagct agacaggctt atcttggaca agaagaagat      780
cgcttggcct cgcgcgcaga tcagttggaa gaatttgtcc actacgtgaa aggcgagatc      840
accaaggtag tcggcaaata aggacgcatg ttacgtctca ccggcgcggg cattgccgaa      900

<210> SEQ ID NO 16
<211> LENGTH: 1849
<212> TYPE: DNA
<213> ORGANISM: Artificial Sequence
<220> FEATURE:
<223> OTHER INFORMATION: C-P lyase knock-out fragment with
      spectinomycin-streptomycin adenyltransferas

<400> SEQUENCE: 16
agctgtaaca ggcgttcagc ctcctgactt aactcataca gggtctgtgt gtacatagaa       60
aattcttcct taaagcaaat tttgttattt tatttagcca gattgttttt gagttctgtt      120
ttcggctttt ataattactg caagaaataa ttttatattt agtgtgttgt ttttatcag       180 aataaataac gtcttctgat acgtttaaaa cgtcagaaag ataaaatat catgtgaatt      240 aaaaaaagaa caagtagagc attaacatta tcttaaataa taaatagagg caaaaagatt      300
attttctttt tgcgtttcct ttcaaatgaa acgatcgtc gtctaaaatc agcagtaccc      360
ccgacaaact cagggatttt tgtgtataatt gcggcctttt tcggcaatct gccgtttttt      420
ggcgcttttg ccctgctgac ttttgaggaa atccacatgt cattaccaca ctgcccaaaa      480
```

```
tgcaactccg aatacaccta cgaagataac ggcatgtaca tctgctaata cgactcacta    540
tagggagaat gagggaagcg gtgatcgccg aagtatcgac tcaactatca gaggtagttg    600
gcgtcatcga gcgccatctc gaaccgacgt tgctggccgt acatttgtac ggctccgcag    660
tggatggcgg cctgaagcca cacagtgata ttgatttgct ggttacggtt acggtgaccg    720
taaggcttga tgaaacaacg cggcgagctt tgatcaacga cctttggaa acttcggctt     780 cccctggaga gagcgagatt ctccgcgctg tagaagtcac cattgttgtg cacgacgaca    840
tcattccgtg gcgttatcca gctaagcgcg aactgcaatt tggagaatgg cagcgcaatg    900
acattcttgc aggtatcttc gagccagcca cgatcgacat tgatctggct atcttgctga    960
caaaagcaag agaacatagc gttgccttgg taggtccagc ggcggaggaa ctctttgatc    1020
cggttcctga acaggatcta tttgaggcgc taaatgaaac cttaacgcta tggaactcgc    1080
cgcccgactg ggctggcgat gagcgaaatg tagtgcttac gttgtcccgc atttggtaca    1140
gcgcagtaac cggcaaaatc gcgccgaagg atgtcgctgc cgactgggca atggagcgcc    1200
tgccggccca gtatcagccc gtcatacttg aagctagaca ggcttatctt ggacaagaag    1260
aagatcgctt ggcctcgcgc gcagatcagt tggaagaatt tgtccactac gtgaaaggcg    1320
agatcaccaa ggtagtcggc aaataaggac gcatgttacg tctcaccggc gcgggcattg    1380
ccgaagaacg aatgatcgcc ccgcagctgc cggagtgcat tctgtacgaa ctcaccgagc    1440
gcccgcaccc gttcccgctc ggcatcgacc tgatcctgac ctgcggcgag cgcctgctgg    1500
ctattccgcg aaccacgcat gtggaggtgt gctgatgtac gttgccgtga agggggcga    1560 aaaggcgatc gatgccgccc acgccctgca agagagccga cgccggggcg ataccgattt    1620
gcctgaactg agcgtcgccc agattgaaca gcagcttaac ctcgcagtag atcgcgtgat    1680
gaccgaaggc ggcattgccg accgcgaact ggcggcgctg gcgctgaaac aggccagcgg    1740
cgataacgtc gaagcaattt tcctgctgcg cgcctaccgc accacgctgg cgaagctcgc    1800
ggtaagcgag ccgctcgaca ccacggagat gcgtctcgaa cggcgtatt               1849
```

<210> SEQ ID NO 17
<211> LENGTH: 1194
<212> TYPE: DNA
<213> ORGANISM: Artificial Sequence
<220> FEATURE:
<223> OTHER INFORMATION: Escherichia coli gemonic fragment 7

<400> SEQUENCE: 17

```
tagttctggt ccggcaatgc taccggcaga ggtgcttaaa caggctcaac aggaactgcg     60
cgactggaac ggtcttggta cgtcggtgat ggaagtgagt caccgtggca agagttcat     120 tcaggttgca gaggaagccg agaaggattt tcgcgatctt cttaatgtcc cctccaacta    180
caaggtatta ttctgccatg gcggtggtcg cggtcagttt gctgcggtac cgctgaatat    240
tctcggtgat aaaaccaccg cagattatgt tgatgccggt tactgggcgg caagtgccat    300
taaagaagcg aaaaaatact gcacgcctaa tgtctttgac gccaaagtga ctgttgatgg    360
tctgcgcgcg gttaagccaa tgcgtgaatg gcaactctct gataatgctg cttatatgca    420
ttactgcccg aatgaaacca tcgacggtat cgccatcgac gaaacgccag acttcggcaa    480
agatgtggtg gtcgccgccg acttctcttc aaccattctt tcccgtccga ttgacgtcag    540
ccgttatggc gtgatttacg ctggcgcgca gaaaaatatc ggcccggctg gcctgacaat    600
cgtcatcgtt cgtgaagatt tgctgggcaa agcgaatatc gcgtgtccgt cgattctgga    660
```

| | |
|---|---|
| ttattccatc ctcaacgata acggctccat gtttaacacg ccgccgacat ttgcctggta | 720 |
| tctatctggt ctggtcttta aatggctgaa agcgaacggc ggtgtagctg aaatggataa | 780 |
| aatcaatcag caaaaagcag aactgctata tggggtgatt gataacagcg atttctaccg | 840 |
| caatgacgtg gcgaaagcta accgttcgcg gatgaacgtg ccgttccagt ggcggacag | 900 |
| tgcgcttgac aaattgttcc ttgaagagtc ttttgctgct ggccttcatg cactgaaagg | 960 |
| tcaccgtgtg gtcggcggaa tgcgcgcttc tatttataac gccatgccgc tggaaggcgt | 1020 |
| taaagcgctg acagacttca tggttgagtt cgaacgccgt cacggttaat gccgaaattt | 1080 |
| tgcttaatcc ccacagccag cctgtggggt ttttatttct gttgtagaga gttgagttca | 1140 |
| tggaatccct gacgttacaa cccatcgctc gtgtcgatgg cactattaat ctgc | 1194 |

<210> SEQ ID NO 18
<211> LENGTH: 1168
<212> TYPE: DNA
<213> ORGANISM: Artificial Sequence
<220> FEATURE:
<223> OTHER INFORMATION: Escherichia coli gemonic fragment 8

<400> SEQUENCE: 18

| | |
|---|---|
| cggattagcc aggcagcctg aatgaacaac gggcaataaa tagccaaatc tttctttatc | 60 |
| aaaacgtcgg cacattgtcg gcgttttttt tcggaccttg tgagtcattt tgattaatgg | 120 |
| tagcgtcgct tgtcaatgta agttgttgat acataatatt tatatatgat taatcaacgg | 180 |
| atgattcaca tgaagaatac taaattactg ctggcgattg cgacctctgc agcattactg | 240 |
| acagggtgtc aaaatacccca cggtattgat accaatatgg ctatcagctc cggtttaaat | 300 |
| gcctataaag cagcaacatt aagcgatgcc gatgcaaaag cgattgccaa tcagggctgt | 360 |
| gccgaaatgg acagcggcaa tcaagtcgca agtaaatcca gcaagtacgg taaacgtctg | 420 |
| gcaaaaatcg ccaaagcatt gggtaacaat attaatggca cgccggtcaa ctataaggtt | 480 |
| tatataacca gcgacgtcaa cgcatgggcg atggcgaacg gctgtgtccg tgtctacagt | 540 |
| ggcctgatgg acatgatgaa tgacaacgaa attgaaggtg ttctgggcca tgaactgggc | 600 |
| cacgtcgcgt tgggtcactc gctggctgaa atgaaagctt cttatgcgat cgttgccgca | 660 |
| cgcgatgcca tttcagctac cagcggtgtg gcttcccagc tttcccgctc acaattgggt | 720 |
| gatatcgcag aaggcgctat taatgctaaa tactcccgtg ataaagagtc cgaagcagat | 780 |
| gatttctcct ttgatctgtt gaagaaacgt ggcatcagca cccaggggct ggttggcagc | 840 |
| tttgaaaaac tggctagtct ggatggcggt cgcacccagt ccatgtttga ctctcaccca | 900 |
| ccatcaacag agcgtgcgca acacatccgt gatcgtatcg cctctggtaa gtaaatcatt | 960 |
| gtcatctttc gggctggtct tctgccagcc cgctataatt gcgcaataaa tccccatctg | 1020 |
| aatacagaca aaactggttt ttgcacacaa cgttaacgat ttgtggcgtc ggcgcgtata | 1080 |
| atgcgcgcgg ttatgttaac ggtacgcctg ttttaaggag ataaagatga cggcaattgc | 1140 |
| cccggttatt accattgatg gcccaagc | 1168 |

<210> SEQ ID NO 19
<211> LENGTH: 1050
<212> TYPE: DNA
<213> ORGANISM: Artificial Sequence
<220> FEATURE:
<223> OTHER INFORMATION: gentamicin 3'-acetyltransferase

<400> SEQUENCE: 19

| | |
|---|---|
| ctgacgttac aacccatcgc tcgtgtcgat ggcactatta atctgcagag gcggtttgcg | 60 |

```
tattgggcgc atgcataaaa actgttgtaa ttcattaagc attctgccga catggaagcc    120
atcacaaacg gcatgatgaa cctgaatcgc cagcggcatc agcaccttgt cgccttgcgt    180
ataatatttg cccatggacg cacaccgtgg aaacggatga aggcacgaac ccagttgaca    240
taagcctgtt cggttcgtaa actgtaatgc aagtagcgta tgcgctcacg caactggtcc    300
agaaccttga ccgaacgcag cggtggtaac ggcgcagtgg cggttttcat ggcttgttat    360
gactgttttt ttgtacagtc tatgcctcgg catccaagc agcaagcgcg ttacgccgtg     420
ggtcgatgtt tgatgttatg gagcagcaac gatgttacgc agcagcaacg atgttacgca    480
gcagggcagt cgccctaaaa caaagttagg tggctcaagt atgggcatca ttcgcacatg    540
taggctcggc cctgaccaag tcaaatccat gcgggctgct cttgatcttt cggtcgtga    600 gttcggagac gtagccacct actcccaaca tcagccggac tccgattacc tcgggaactt    660
gctccgtagt aagacattca tcgcgcttgc tgccttcgac caagaagcgg ttgttggcgc    720
tctcgcggct tacgttctgc ccaagtttga gcagccgcgt agtgagatct atatctatga    780
tctcgcagtc tccggagagc accggaggca gggcattgcc accgcgctca tcaatctcct    840
caagcatgag gccaacgcgc ttggtgctta tgtgatctac gtgcaagcag attacggtga    900
cgatcccgca gtggctctct atacaaagtt gggcatacgg aagaagtga tgcactttga    960 tatcgaccca gtaccgcca cctaacaatt cgttcaagcc gagatccgga ttagccaggc    1020
agcctgaatg aacaacgggc aataaatagc                                   1050

<210> SEQ ID NO 20
<211> LENGTH: 3322
<212> TYPE: DNA
<213> ORGANISM: Artificial Sequence
<220> FEATURE:
<223> OTHER INFORMATION: EPSPS knock-out fragment with gentamicin 3'-
      acetyltransferase

<400> SEQUENCE: 20
tagttctggt ccggcaatgc taccggcaga ggtgcttaaa caggctcaac aggaactgcg    60
cgactggaac ggtcttggta cgtcggtgat ggaagtgagt caccgtggca aagagttcat    120
tcaggttgca gaggaagccg agaaggattt tcgcgatctt cttaatgtcc cctccaacta    180
caaggtatta ttctgccatg gcggtggtcg cggtcagttt gctgcggtac cgctgaatat    240
tctcggtgat aaaaccaccg cagattatgt tgatgccggt tactgggcgg caagtgccat    300
taaagaagcg aaaaaatact gcacgcctaa tgtctttgac gccaaagtga ctgttgatgg    360
tctgcgcgcg gttaagccaa tgcgtgaatg gcaactctct gataatgctg cttatatgca    420
ttactgcccg aatgaaacca tcgacggtat cgccatcgac gaaacgccag acttcggcaa    480
agatgtggtg gtcgccgccg acttctcttc aaccattctt tcccgtccga ttgacgtcag    540
ccgttatggc gtgatttacg ctggcgcgca gaaaaatatc ggcccggctg gcctgacaat    600
cgtcatcgtt cgtgaagatt tgctgggcaa agcgaatatc gcgtgtccgt cgattctgga    660
ttattccatc ctcaacgata acggctccat gtttaacacg ccgccgacat tgcctggta    720 tctatctggt ctggtctta aatggctgaa agcgaacggc ggtgtagctg aaatggataa    780
aatcaatcag caaaaagcag aactgctata tgggtgatt gataacagcg atttctaccg    840
caatgacgtg gcgaaagcta accgttcgcg gatgaacgtg ccgttccagt ggcggacag    900 tgcgcttgac aaattgttcc ttgaagagtc ttttgctgct ggccttcatg cactgaaagg    960
tcaccgtgtg gtcggcggaa tgcgcgcttc tatttataac gccatgccgc tggaaggcgt    1020
```

```
taaagcgctg acagacttca tggttgagtt cgaacgccgt cacgttaat gccgaaattt   1080 tgcttaatcc ccacagccag cctgtggggt ttttatttct gttgtagaga gttgagttca   1140
tggaatccct gacgttacaa cccatcgctc gtgtcgatgg cactattaat ctgcagaggc   1200
ggtttgcgta ttgggcgcat gcataaaaac tgttgtaatt cattaagcat tctgccgaca   1260
tggaagccat cacaaacggc atgatgaacc tgaatcgcca gcggcatcag caccttgtcg   1320
ccttgcgtat aatatttgcc catgacgca caccgtggaa acggatgaag cacgaaccc   1380 agttgacata agcctgttcg gttcgtaaac tgtaatgcaa gtagcgtatg cgctcacgca   1440
actggtccag aaccttgacc gaacgcagcg gtggtaacgg cgcagtggcg gttttcatgg   1500
cttgttatga ctgttttttt gtacagtcta tgcctcgggc atccaagcag caagcgcgtt   1560
acgccgtggg tcgatgtttg atgttatgga gcagcaacga tgttacgcag cagcaacgat   1620
gttacgcagc agggcagtcg ccctaaaaca aagttaggtg gctcaagtat gggcatcatt   1680
cgcacatgta ggctcggccc tgaccaagtc aaatccatgc gggctgctct tgatcttttc   1740
ggtcgtgagt tcggagacgt agccacctac tcccaacatc agccggactc cgattacctc   1800
gggaacttgc tccgtagtaa gacattcatc gcgcttgctg ccttcgacca agaagcggtt   1860
gttggcgctc tcgcggctta cgttctgccc aagtttgagc agccgcgtag tgagatctat   1920
atctatgatc tcgcagtctc cggagagcac cggaggcagg gcattgccac cgcgctcatc   1980
aatctcctca agcatgaggc caacgcgctt ggtgcttatg tgatctacgt gcaagcagat   2040
tacggtgacg atcccgcagt ggctctctat acaaagttgg gcatacggga agaagtgatg   2100
cactttgata tcgacccaag taccgccacc taacaattcg ttcaagccga tccggatt   2160 agccaggcag cctgaatgaa caacgggcaa taaatagcca aatctttctt tatcaaaacg   2220
tcggcacatt gtcggcgttt tttttcggac cttgtgagtc attttgatta atggtagcgt   2280
cgcttgtcaa tgtaagttgt tgatacataa tatttatata tgattaatca acggatgatt   2340
cacatgaaga atactaaatt actgctggcg attgcgacct ctgcagcatt actgacaggg   2400
tgtcaaaata cccacggtat tgataccaat atggctatca gctccggttt aaatgcctat   2460
aaagcagcaa cattaagcga tgccgatgca aaagcgattg ccaatcaggg ctgtgccgaa   2520
atggacagcg gcaatcaagt cgcaagtaaa tccagcaagt acggtaaacg tctggcaaaa   2580
atcgccaaag cattgggtaa caatattaat ggcacgccgg tcaactataa ggtttatata   2640
accagcgacg tcaacgcatg ggcgatggcg aacggctgtg tccgtgtcta cagtggcctg   2700
atggacatga tgaatgacaa cgaaattgaa ggtgttctgg gccatgaact gggccacgtc   2760
gcgttgggtc actcgctggc tgaaatgaaa gcttcttatg cgatcgttgc cgcacgcgat   2820
gccatttcag ctaccagcgg tgtggcttcc cagctttccc gctcacaatt gggtgatatc   2880
gcagaaggcg ctattaatgc taaatactcc cgtgataaag agtccgaagc agatgatttc   2940
tcctttgatc tgttgaagaa acgtggcatc agcacccagg gctggttgg cagctttgaa   3000 aaactggcta gtctggatgg cggtcgcacc cagtccatgt ttgactctca cccaccatca   3060
acagagcgtg cgcaacacat ccgtgatcgt atcgcctctg gtaagtaaat cattgtcatc   3120
tttcgggctg gtcttctgcc agcccgctat aattgcgcaa taaatcccca tctgaataca   3180
gacaaaactg gttttttgcac acaacgttaa cgatttgtgg cgtcggcgcg tataatgcgc   3240
gcggttatgt taacggtacg cctgttttaa ggagataaag atgacggcaa ttgccccggt   3300
tattaccatt gatggcccaa gc                                           3322
```

<210> SEQ ID NO 21
<211> LENGTH: 1586
<212> TYPE: DNA
<213> ORGANISM: Artificial Sequence
<220> FEATURE:
<223> OTHER INFORMATION: Escherichia coli gemonic fragment 9

<400> SEQUENCE: 21

```
ccgaccagct acccaacacg ctatcaagag atagccgcaa aacttgagca ggagcttcgt      60
caacactacc gctgcggcga ctatcttccc gccgagcagc aactggcagc gcgctttgag     120
gtgaatcgcc acaccctgcg ccgcgccatc gaccaactgg tggaaaaagg ctgggtacag     180
cgccgtcagg gcgtctgcgt cgactctaga ggatcccggg aggcctggtg cgcataatgt     240
atattatgtt aaatagaggc ggtttgcgta ttgggcgcat gcataaaaac tgttgtaatt     300
cattaagcat tctgccgaca tggaagccat cacaaacggc atgatgaacc tgaatcgcca     360
gcggcatcag caccttgtcg ccttgcgtat aatatttgcc catggacgca caccgtggaa     420
acggatgaag gcacgaaccc agttgacata agcctgttcg gttcgtaaac tgtaatgcaa     480
gtagcgtatg cgctcacgca actggtccag aaccttgacc gaacgcagcg gtggtaacgg     540
cgcagtggcg gttttcatgg cttgttatga ctgtttttt gtacagtcta tgcctcgggc     600
atccaagcag caagcgcgtt acgccgtggg tcgatgtttg atgttatgga gcagcaacga     660
tgttacgcag cagcaacgat gttacgcagc agggcagtcg ccctaaaaca agttaggtg      720
gctcaagtat gggcatcatt cgcacatgta ggctcggccc tgaccaagtc aaatccatgc     780
gggctgctct tgatcttttc ggtcgtgagt tcggagacgt agccacctac tcccaacatc     840
agccggactc cgattacctc gggaacttgc tccgtagtaa gacattcatc gcgcttgctg     900
ccttcgacca agaagcggtt gttggcgctc tcgcggctta cgttctgccc aagtttgagc     960
agccgcgtag tgagatctat atctatgatc tcgcagtctc cggagagcac cggaggcagg    1020
gcattgccac cgcgctcatc aatctcctca agcatgaggc caacgcgctt ggtgcttatg    1080
tgatctacgt gcaagcagat tacggtgacg atcccgcagt ggctctctat acaaagttgg    1140
gcatacggga agaagtgatg cactttgata tcgacccaag taccgccacc taacaattcg    1200
ttcaagccga gatcggcttg gtgcgcataa tgtatattat gttaaatccc gggtaccgag    1260
ctcgaattct cagaattgcc ttcgcggtga cggatgaggc gatttccagc gaacagctca    1320
acgcccttc caccggcacc gccgttgcgc cggaagcggg tgcgacgctg attttacagg     1380
tcgccagcct gagcggcgga cgcatgttgc gccttactgg tgcgggtatt gccgaagaac    1440
gaatgatcgc tccgcagctg ccggagtgca ttctgcacga actcaccgag cgcccgcatc    1500
cgttcccgct cggcatcgac ctgatcctga cctgtggcga gcgcctgctg gctattccgc    1560
gaaccactca tgtggaggtg tgctga                                         1586
```

<210> SEQ ID NO 22
<211> LENGTH: 1607
<212> TYPE: DNA
<213> ORGANISM: Artificial Sequence
<220> FEATURE:
<223> OTHER INFORMATION: Escherichia coli gemonic fragment 10

<400> SEQUENCE: 22

```
tccctgacgt tacaacccat cgctcgtgtc gatggcacta ttaatctgcc cggttccaag      60
agcgtttcta accgcgcttt attgctggcg gcattagcac acggcaaaac agtattaacc     120
aatctgctgg atagcgatga cgtgcgccat atgctgaatg cattaacagc gttagggta      180
```

```
agctatacgc tttcagccga tcgtacgcgt tgcgaaatta tcggtaacgg cggtccatta    240
ctccagggca ccttctgcgt gggggatcct ctagagtcga cgcagggagg cctggtgcgc    300
ataatgtata ttatgttaaa tagaggcggt ttgcgtattg ggcgcatgca taaaaactgt    360
tgtaattcat taagcattct gccgacatgg aagccatcac aaacggcatg atgaacctga    420
atcgccagcg gcatcagcac cttgtcgcct tgcgtataat atttgcccat ggacgcacac    480
cgtggaaacg gatgaaggca cgaacccagt tgacataagc ctgttcggtt cgtaaactgt    540
aatgcaagta gcgtatgcgc tcacgcaact ggtccagaac cttgaccgaa cgcagcggtg    600
gtaacggcgc agtggcggtt ttcatggctt gttatgactg ttttttttgta cagtctatgc    660 ctcgggcatc caagcagcaa gcgcgttacg ccgtgggtcg atgtttgatg ttatggagca    720
gcaacgatgt tacgcagcag caacgatgtt acgcagcagg cagtcgccc taaaacaaag    780 ttaggtggct caagtatggg catcattcgc acatgtaggc tcggccctga ccaagtcaaa    840
tccatgcggg ctgctcttga tcttttcggt cgtgagttcg gagacgtagc cacctactcc    900
caacatcagc cggactccga ttacctcggg aacttgctcc gtagtaagac attcatcgcg    960
cttgctgcct tcgaccaaga agcggttgtt ggcgctctcg cggcttacgt tctgcccaag   1020
tttgagcagc cgcgtagtga gatctatatc tatgatctcg cagtctccgg agagcaccgg   1080
aggcagggca ttgccaccgc gctcatcaat ctcctcaagc atgaggccaa cgcgcttggt   1140
gcttatgtga tctacgtgca agcagattac ggtgacgatc ccgcagtggc tctctataca   1200
aagttgggca tacgggaaga agtgatgcac tttgatatcg acccaagtac cgccacctaa   1260
caattcgttc aagccgagat cggcttggtg cgcataatgt atattatgtt aaatcccggg   1320
gtaccgagct cgaattctca gaattgcgac catttgctgg ggcgatgatt atatttcctg   1380
cacgcgtggt gaactgaacg ctattgatat ggatatgaac catattcctg atgcggcgat   1440
gaccattgcc acggcggcgt tatttgcaaa aggcaccacc acgctgcgca atatctataa   1500
ctggcgtgtt aaagagaccg atcgcctgtt tgcgatggca acagaactgc gtaaagtcgg   1560
cgcggaagtg aagagggggc accggaggag tgatacgaat gtaatcg                 1607

<210> SEQ ID NO 23
<211> LENGTH: 24
<212> TYPE: DNA
<213> ORGANISM: Artificial Sequence
<220> FEATURE:
<223> OTHER INFORMATION: PRIMER

<400> SEQUENCE: 23
agctgtaaca ggcgttcagc ctcc                                            24

<210> SEQ ID NO 24
<211> LENGTH: 24
<212> TYPE: DNA
<213> ORGANISM: Artificial Sequence
<220> FEATURE:
<223> OTHER INFORMATION: PRIMER

<400> SEQUENCE: 24
gcagatgtac atgccgttat cttc                                            24

<210> SEQ ID NO 25
<211> LENGTH: 23
<212> TYPE: DNA
<213> ORGANISM: Artificial Sequence
<220> FEATURE:
```

```
<223> OTHER INFORMATION: PRIMER

<400> SEQUENCE: 25
ggacgcatgt tacgtctcac cgg                                            23

<210> SEQ ID NO 26
<211> LENGTH: 24
<212> TYPE: DNA
<213> ORGANISM: Artificial Sequence
<220> FEATURE:
<223> OTHER INFORMATION: PRIMER

<400> SEQUENCE: 26
aatacgccgt tcgagacgca tctc                                           24

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
gcccagtatc agcccgtcat acttg                                          25

<210> SEQ ID NO 28
<211> LENGTH: 24
<212> TYPE: DNA
<213> ORGANISM: Artificial Sequence
<220> FEATURE:
<223> OTHER INFORMATION: PRIMER

<400> SEQUENCE: 28
ctcatgccga ataccagccc gtag                                           24

<210> SEQ ID NO 29
<211> LENGTH: 66
<212> TYPE: DNA
<213> ORGANISM: Artificial Sequence
<220> FEATURE:
<223> OTHER INFORMATION: PRIMER

<400> SEQUENCE: 29
ctccgaatac acttacgaag ataacggcat gtacatctgc taatacgact cactataggg    60
agaatg                                                               66

<210> SEQ ID NO 30
<211> LENGTH: 62
<212> TYPE: DNA
<213> ORGANISM: Artificial Sequence
<220> FEATURE:
<223> OTHER INFORMATION: PRIMER

<400> SEQUENCE: 30
cttcggcaat gcccgcgccg gtgagacgta acatgcgtcc ttatttgccg actaccttgg    60
tg                                                                   62

<210> SEQ ID NO 31
<211> LENGTH: 24
<212> TYPE: DNA
<213> ORGANISM: Artificial Sequence
<220> FEATURE:
<223> OTHER INFORMATION: PRIMER

<400> SEQUENCE: 31
```

```
tagttctggt ccggcaatgc tacc                                              24

<210> SEQ ID NO 32
<211> LENGTH: 25
<212> TYPE: DNA
<213> ORGANISM: Artificial Sequence
<220> FEATURE:
<223> OTHER INFORMATION: PRIMER

<400> SEQUENCE: 32
gcagattaat agtgccatcg acacg                                             25

<210> SEQ ID NO 33
<211> LENGTH: 24
<212> TYPE: DNA
<213> ORGANISM: Artificial Sequence
<220> FEATURE:
<223> OTHER INFORMATION: PRIMER

<400> SEQUENCE: 33
cggattagcc aggcagcctg aatg                                              24

<210> SEQ ID NO 34
<211> LENGTH: 25
<212> TYPE: DNA
<213> ORGANISM: Artificial Sequence
<220> FEATURE:
<223> OTHER INFORMATION: PRIMER

<400> SEQUENCE: 34
gcttgggcca tcaatggtaa taacc                                             25

<210> SEQ ID NO 35
<211> LENGTH: 70
<212> TYPE: DNA
<213> ORGANISM: Artificial Sequence
<220> FEATURE:
<223> OTHER INFORMATION: PRIMER

<400> SEQUENCE: 35
ctgacgttac aacccatcgc tcgtgtcgat ggcactatta atctgcagag gcggtttgcg       60
tattgggcgc                                                              70

<210> SEQ ID NO 36
<211> LENGTH: 70
<212> TYPE: DNA
<213> ORGANISM: Artificial Sequence
<220> FEATURE:
<223> OTHER INFORMATION: PRIMER

<400> SEQUENCE: 36
gctatttatt gcccgttgtt cattcaggct gcctggctaa tccgtgatct cggcttgaac       60
gaattgttag                                                              70

<210> SEQ ID NO 37
<211> LENGTH: 25
<212> TYPE: DNA
<213> ORGANISM: Artificial Sequence
<220> FEATURE:
<223> OTHER INFORMATION: PRIMER

<400> SEQUENCE: 37
tgattatatt tcctgcacgc gtggt                                             25
```

<210> SEQ ID NO 38
<211> LENGTH: 24
<212> TYPE: DNA
<213> ORGANISM: Artificial Sequence
<220> FEATURE:
<223> OTHER INFORMATION: PRIMER

<400> SEQUENCE: 38
tgagcgcaac gcaattaatg tgag                                              24

<210> SEQ ID NO 39
<211> LENGTH: 25
<212> TYPE: DNA
<213> ORGANISM: Artificial Sequence
<220> FEATURE:
<223> OTHER INFORMATION: PRIMER

<400> SEQUENCE: 39
cgtaaggaga aataccgca tcagg                                              25

<210> SEQ ID NO 40
<211> LENGTH: 40
<212> TYPE: DNA
<213> ORGANISM: Artificial Sequence
<220> FEATURE:
<223> OTHER INFORMATION: PRIMER

<400> SEQUENCE: 40
ttacgtacgt taattaatgg cgtccaacgc cgcggctgcg                             40

<210> SEQ ID NO 41
<211> LENGTH: 46
<212> TYPE: DNA
<213> ORGANISM: Artificial Sequence
<220> FEATURE:
<223> OTHER INFORMATION: PRIMER

<400> SEQUENCE: 41
ttacgtacgt cctgcaggtc agttcctgac gaaagtgctt agaacg                      46

<210> SEQ ID NO 42
<211> LENGTH: 25
<212> TYPE: DNA
<213> ORGANISM: Artificial Sequence
<220> FEATURE:
<223> OTHER INFORMATION: PRIMER

<400> SEQUENCE: 42
ccgaccagct acccaacacg ctatc                                             25

<210> SEQ ID NO 43
<211> LENGTH: 43
<212> TYPE: DNA
<213> ORGANISM: Artificial Sequence
<220> FEATURE:
<223> OTHER INFORMATION: PRIMER

<400> SEQUENCE: 43
ggggatcctc tagagtcgac gcagacgccc tgacggcgct gta                         43

<210> SEQ ID NO 44
<211> LENGTH: 49
<212> TYPE: DNA
<213> ORGANISM: Artificial Sequence
<220> FEATURE:
<223> OTHER INFORMATION: PRIMER -continued

<400> SEQUENCE: 44
gggtaccgag ctcgaattct cagaattgcc ttcgcggtga cggatgagg            49

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
tcagcacacc tccacatgag tggttc                                     26

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
tgctggattt cctctctcaa cg                                         22

<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47
atttaacata atatacatta tgcgcacc                                   28

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
gctatcctct tcaaacttcg ccagc                                      25

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
tccctgacgt tacaacccat cgc                                        23

<210> SEQ ID NO 50
<211> LENGTH: 44
<212> TYPE: DNA
<213> ORGANISM: Artificial Sequence
<220> FEATURE:
<223> OTHER INFORMATION: Primer

<400> SEQUENCE: 50
ggggatcctc tagagtcgac gcactccagg gcaccttctg cgtg                 44

<210> SEQ ID NO 51

```
<211> LENGTH: 46
<212> TYPE: DNA
<213> ORGANISM: Artificial Sequence
<220> FEATURE:
<223> OTHER INFORMATION: Primer

<400> SEQUENCE: 51
ggtaccgagc tcgaattctc agaattgcga ccatttgctg gggcga                          46

<210> SEQ ID NO 52
<211> LENGTH: 25
<212> TYPE: DNA
<213> ORGANISM: Artificial Sequence
<220> FEATURE:
<223> OTHER INFORMATION: primer

<400> SEQUENCE: 52
cggaggagtg atacgaatgt aatcg                                                 25

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
gcgctgacag acttcatggt tg                                                    22

<210> SEQ ID NO 54
<211> LENGTH: 23
<212> TYPE: DNA
<213> ORGANISM: Artificial Sequence
<220> FEATURE:
<223> OTHER INFORMATION: primer

<400> SEQUENCE: 54
caacttacat tgacaagcga cgc                                                   23
```